US009820878B2

(12) United States Patent
Parker, Jr. et al.

(10) Patent No.: US 9,820,878 B2
(45) Date of Patent: Nov. 21, 2017

(54) EVERTING DEPLOYMENT SYSTEM AND HANDLE

(71) Applicant: Cook Medical Technologies LLC, Bloomington, IN (US)

(72) Inventors: Fred T Parker, Jr., Unionville, IN (US); Palle M Hansen, Bjaeverskov (DK)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 20 days.

(21) Appl. No.: 14/632,615

(22) Filed: Feb. 26, 2015

(65) Prior Publication Data

US 2015/0164669 A1 Jun. 18, 2015

Related U.S. Application Data

(62) Division of application No. 13/264,331, filed as application No. PCT/US2010/030696 on Apr. 12, 2010, now Pat. No. 8,968,381.

(Continued)

(51) Int. Cl.
*A61F 2/97* (2013.01)
*A61F 2/95* (2013.01)
(Continued)

(52) U.S. Cl.
CPC ............... *A61F 2/97* (2013.01); *A61F 2/95* (2013.01); *A61F 2/966* (2013.01); *A61L 29/085* (2013.01);
(Continued)

(58) Field of Classification Search
CPC .... A61F 2/97; A61F 2/95; A61F 2/966; A61F 2002/9517; A61F 2002/9522; A61L 29/085
See application file for complete search history.

(56) References Cited

U.S. PATENT DOCUMENTS

| 5,350,101 A | 9/1994 | Godlewski |
| 5,380,304 A | 1/1995 | Parker |

(Continued)

FOREIGN PATENT DOCUMENTS

| EP | 1 844 739 A1 | 10/2007 |
| WO | WO 2004/030571 A2 | 4/2004 |

(Continued)

OTHER PUBLICATIONS

Search Report for related PCT Application No. PCT/US2010/030696, dated Aug. 31, 2010.

*Primary Examiner* — Jocelin Tanner
(74) *Attorney, Agent, or Firm* — Brinks Gilson & Lione

(57) ABSTRACT

A stent deployment system, handle, and method of loading of a medical device are provided. The system includes an outer catheter having an inner liner extending past the end of the outer catheter and an inner catheter disposed within the outer catheter. The inner liner is inverted and attached to the inner catheter. Relative movement between the outer and the inner catheters can urge the inner liner to peel away from the medical device. A handle is disposed at the proximal end of the outer catheter, and may include a splitter configured to slice the wall of the tubular member. The handle may also include a rotatable mechanism that can be attached to the tubular member. Rotation of the rotatable mechanism retracts a portion of the tubular member into the handle and winds the sliced portion about the rotatable mechanism.

15 Claims, 22 Drawing Sheets

Related U.S. Application Data

(60) Provisional application No. 61/169,590, filed on Apr. 15, 2009.

(51) Int. Cl.
*A61F 2/966* (2013.01)
*A61L 29/08* (2006.01)

(52) U.S. Cl.
CPC ............. *A61F 2002/9517* (2013.01); *A61F 2002/9522* (2013.01); *A61F 2250/0039* (2013.01)

(56) References Cited

U.S. PATENT DOCUMENTS

| | | | |
|---|---|---|---|
| 5,662,703 A | 9/1997 | Yurek et al. | |
| 5,690,644 A | 11/1997 | Yurek et al. | |
| 5,782,811 A | 7/1998 | Samson et al. | |
| 5,972,143 A | 10/1999 | Stevens | |
| 6,254,628 B1 | 7/2001 | Wallace et al. | |
| 6,673,101 B1 | 1/2004 | Fitzgerald et al. | |
| 6,709,454 B1 | 3/2004 | Cox et al. | |
| 6,979,339 B2 * | 12/2005 | Bishop | A61B 17/435 604/264 |
| 7,238,197 B2 | 7/2007 | Sequin et al. | |
| 7,326,236 B2 | 2/2008 | Andreas et al. | |
| 2002/0032408 A1 | 3/2002 | Parker et al. | |
| 2002/0099431 A1 | 7/2002 | Armstrong et al. | |
| 2002/0123755 A1 * | 9/2002 | Lowe | A61F 2/01 606/108 |
| 2002/0173809 A1 | 11/2002 | Fleischman et al. | |
| 2003/0050686 A1 | 3/2003 | Raeder-Devens et al. | |
| 2004/0143272 A1 | 7/2004 | Cully et al. | |
| 2004/0260333 A1 | 12/2004 | Dubrul et al. | |
| 2005/0090890 A1 | 4/2005 | Wu et al. | |
| 2006/0015171 A1 | 1/2006 | Armstrong | |
| 2006/0111771 A1 | 5/2006 | Ton et al. | |
| 2006/0135981 A1 | 6/2006 | Lenker et al. | |
| 2006/0200110 A1 | 9/2006 | Lentz et al. | |
| 2006/0259118 A1 | 11/2006 | Pal et al. | |
| 2007/0010867 A1 | 1/2007 | Carter et al. | |
| 2007/0208350 A1 | 9/2007 | Gunderson | |
| 2007/0219617 A1 | 9/2007 | Saint | |
| 2007/0244540 A1 * | 10/2007 | Pryor | A61F 2/95 623/1.11 |
| 2008/0300574 A1 * | 12/2008 | Belson | A61M 25/0606 604/510 |
| 2009/0270969 A1 * | 10/2009 | Fargahi | A61F 2/95 623/1.11 |
| 2010/0049168 A1 * | 2/2010 | Parker | A61M 25/0053 604/527 |
| 2010/0174290 A1 * | 7/2010 | Wuebbeling | A61F 2/95 606/108 |

FOREIGN PATENT DOCUMENTS

| WO | WO 2008/124844 A1 | 10/2008 |
|---|---|---|
| WO | WO 2010/120620 A1 | 10/2010 |

\* cited by examiner

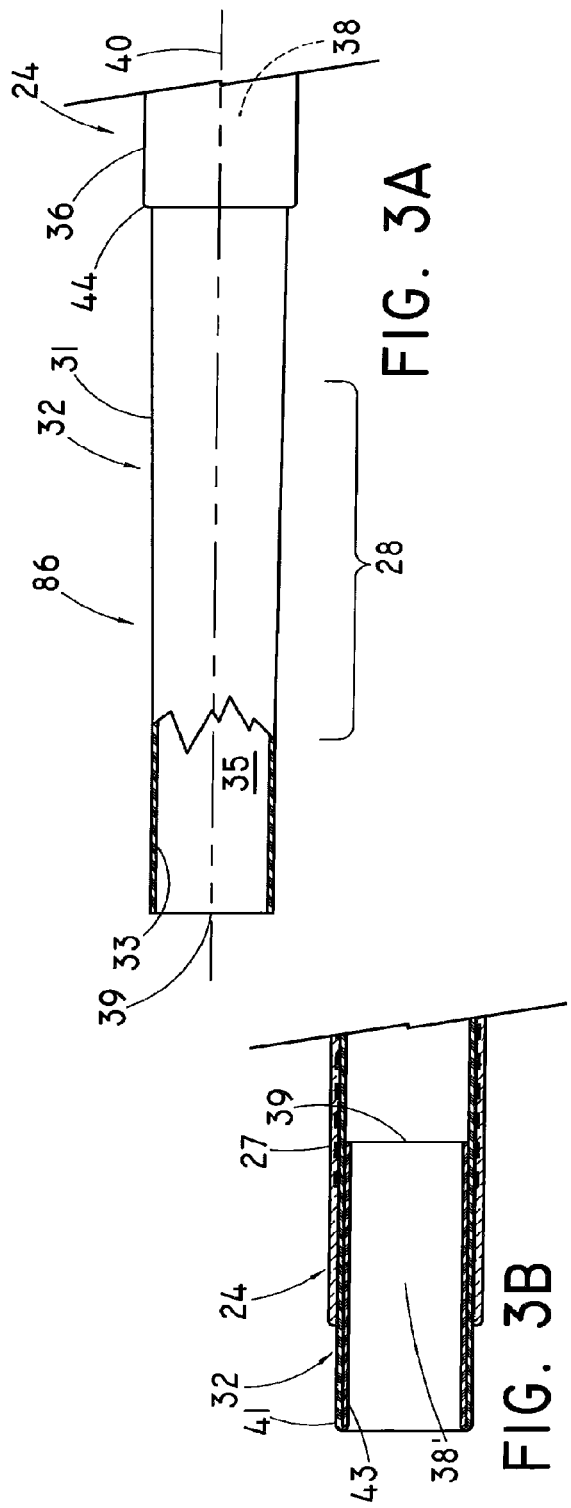
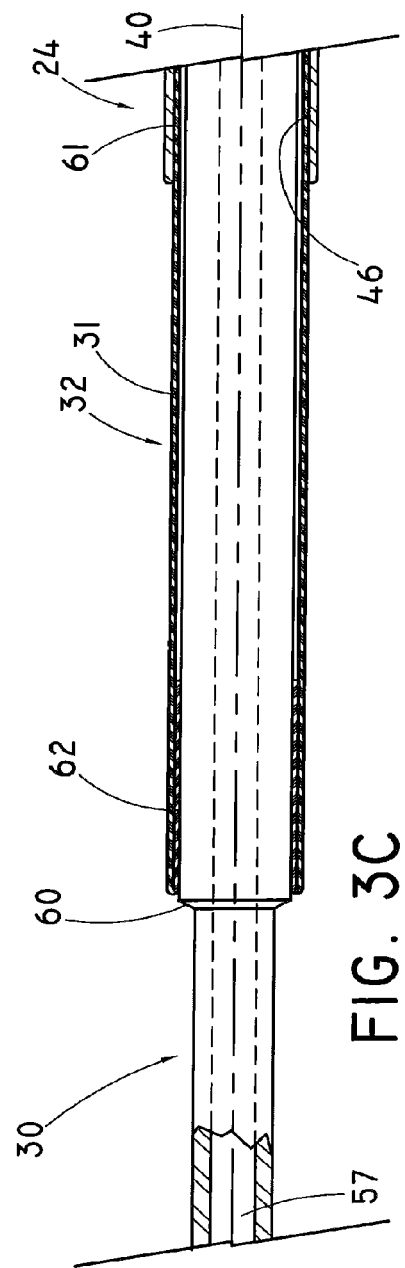
FIG. 3A
FIG. 3B
FIG. 3C

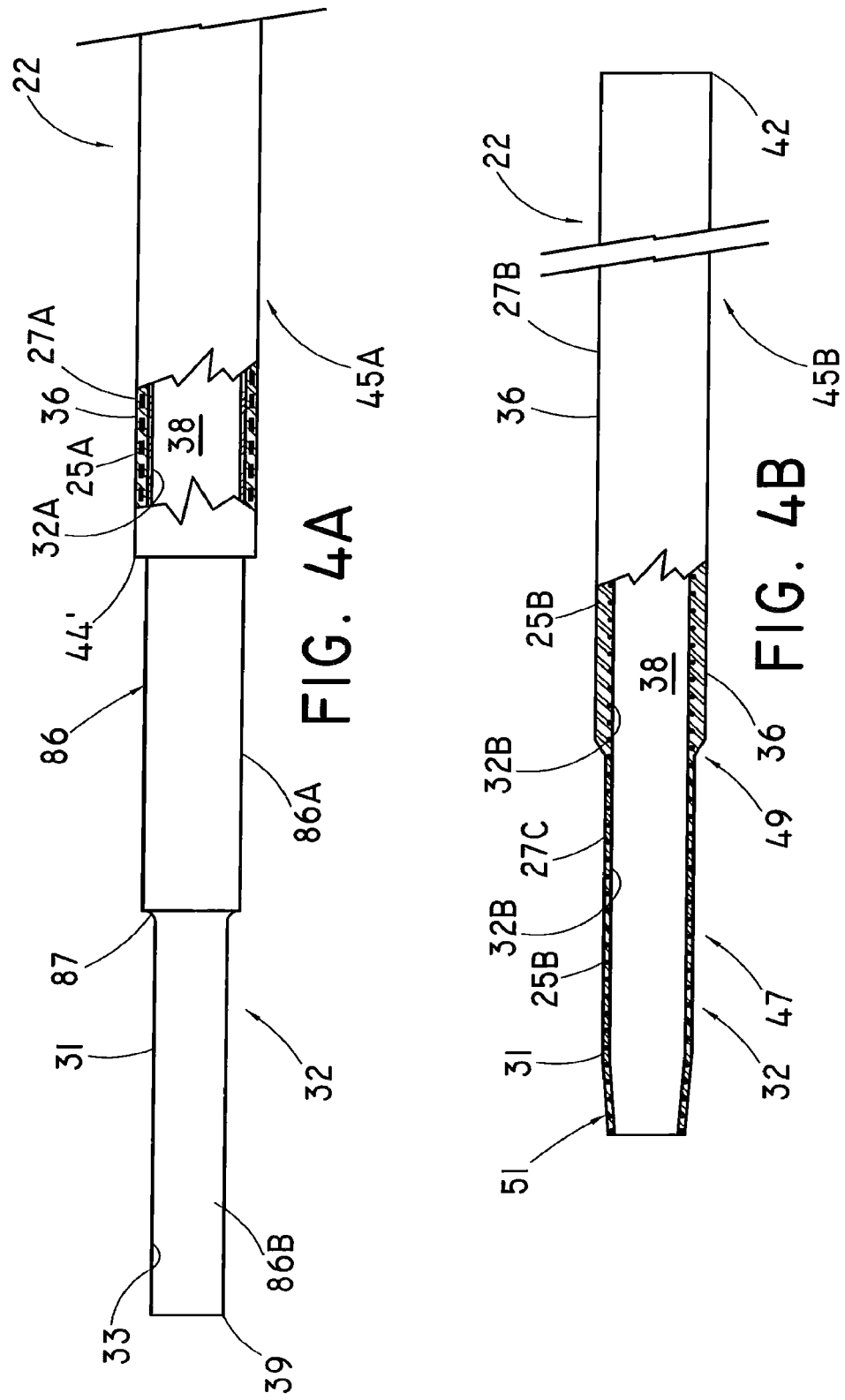

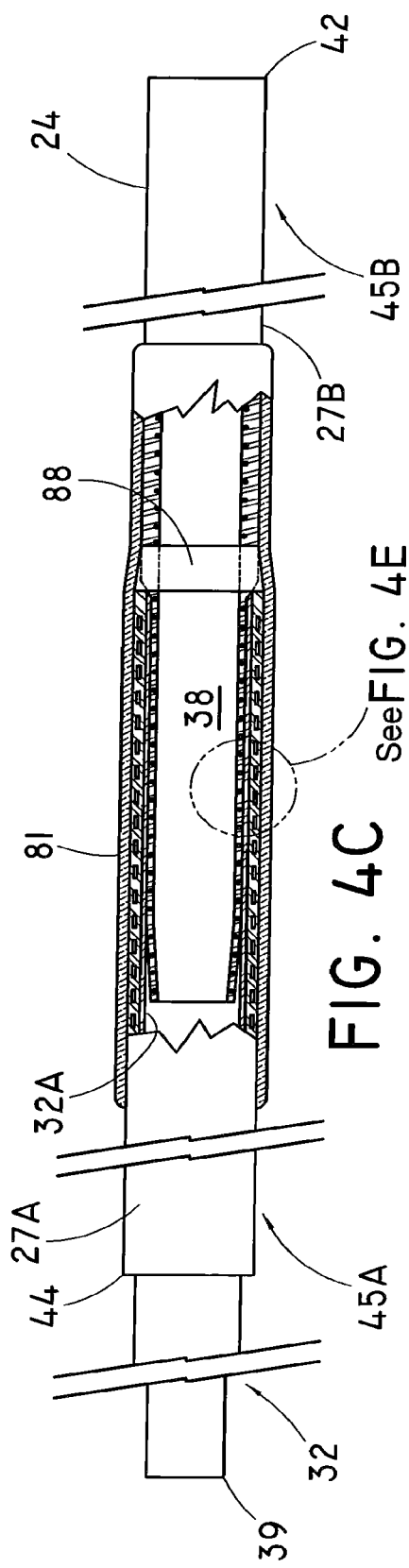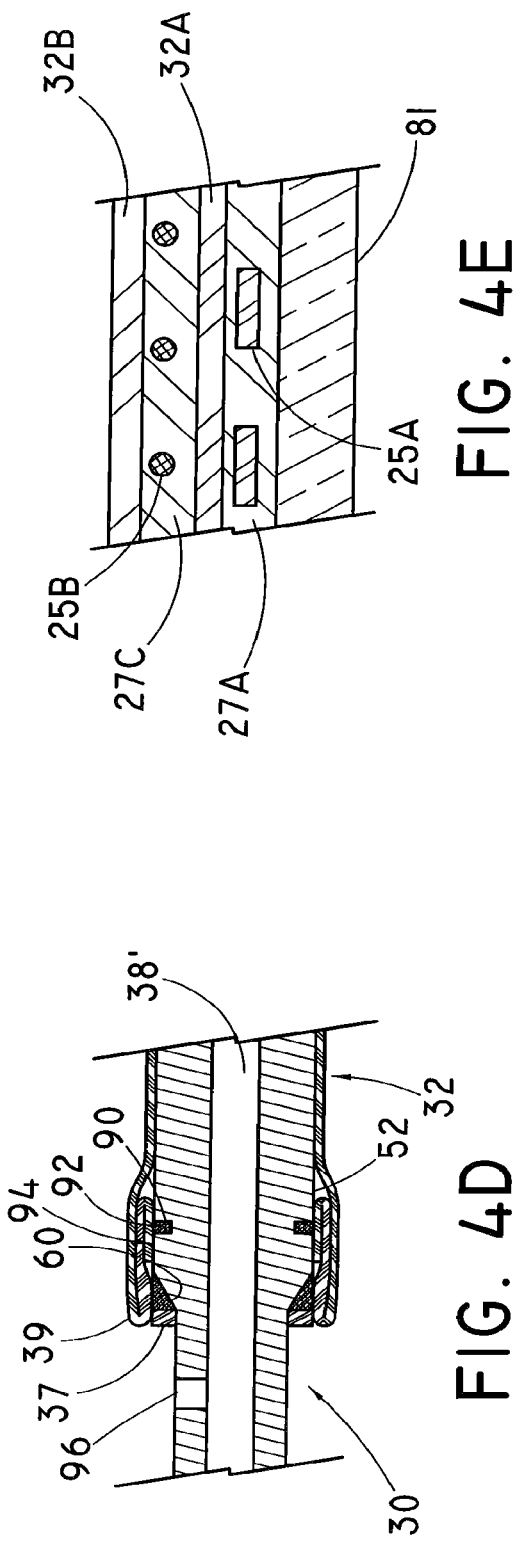

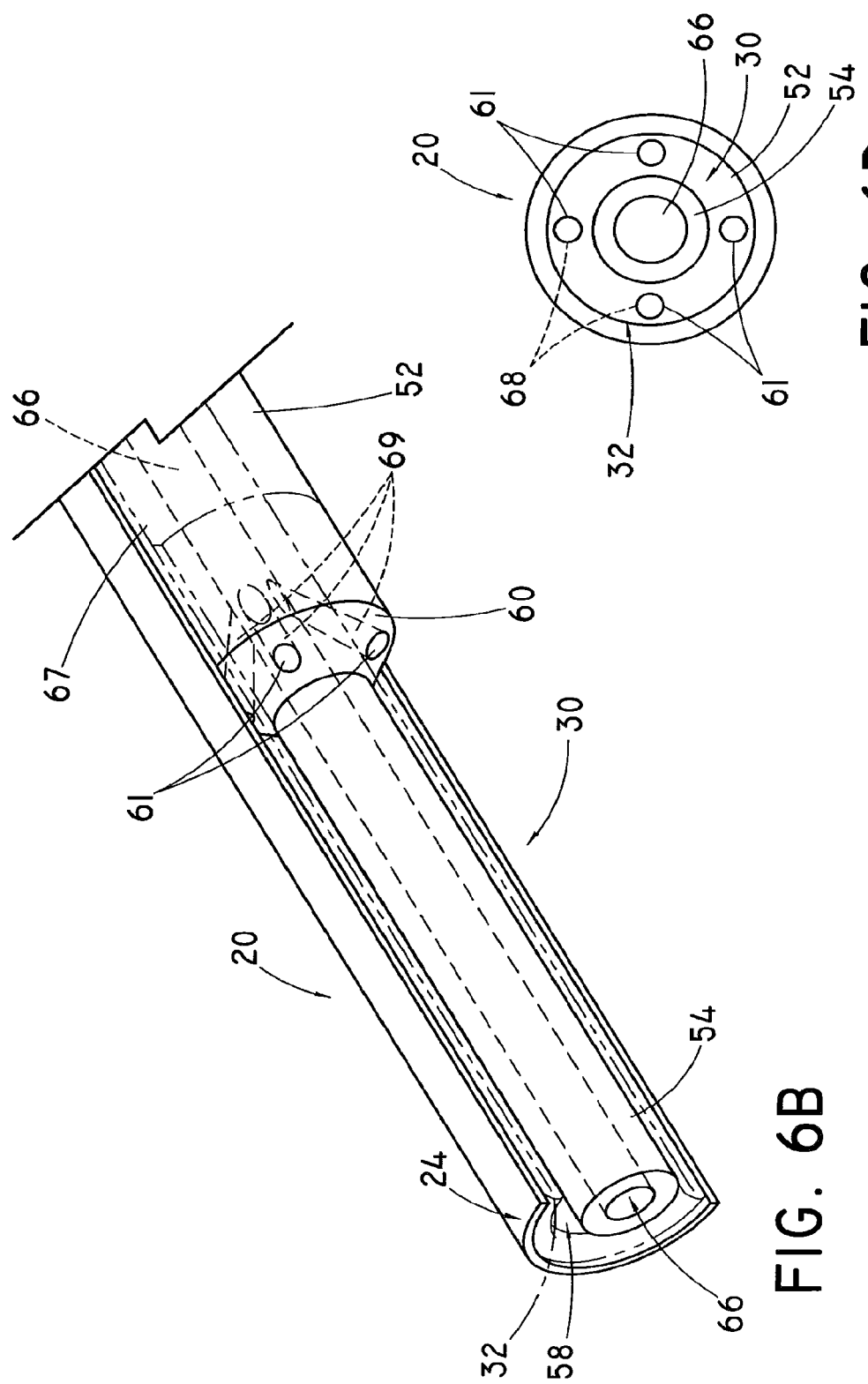

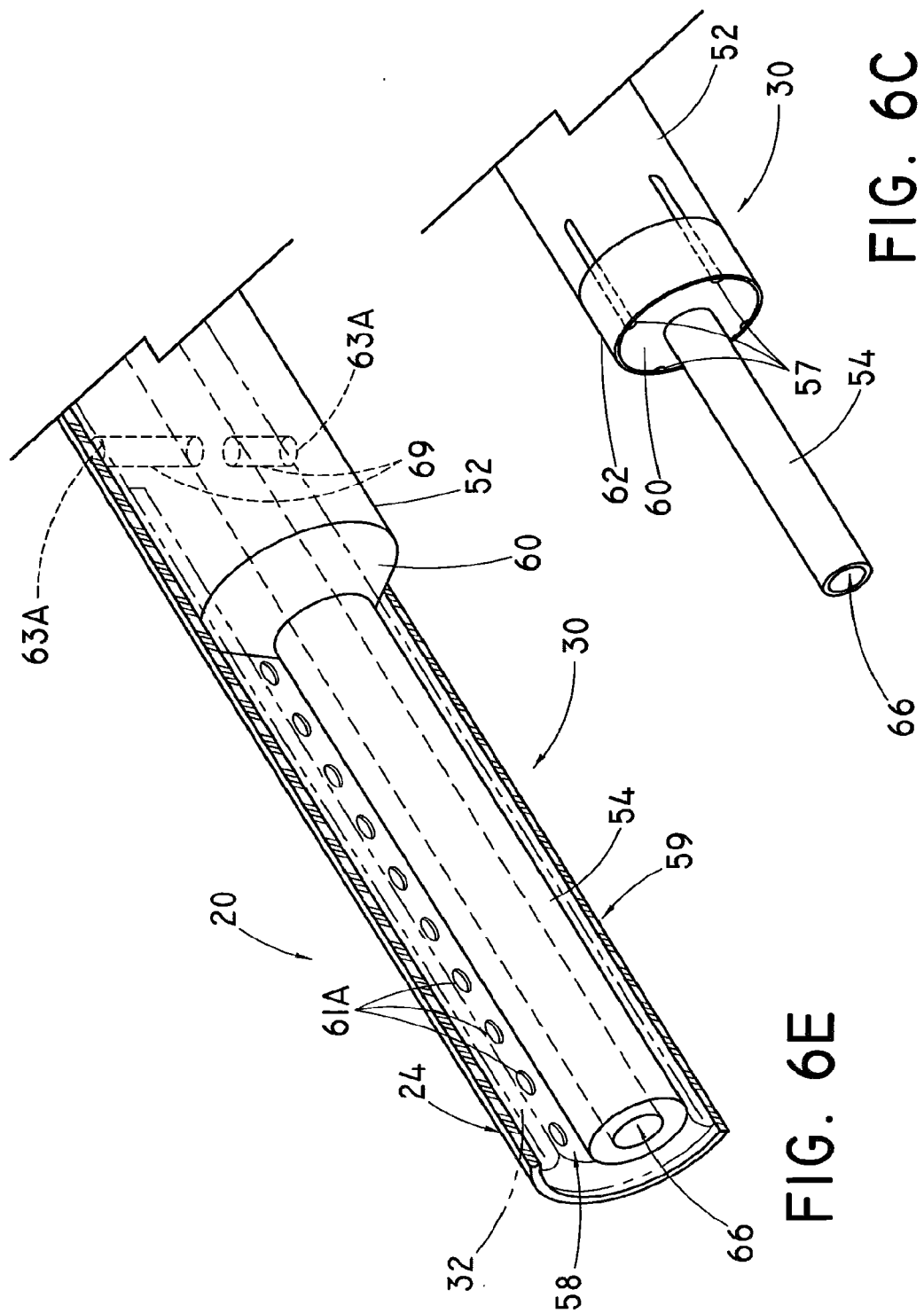

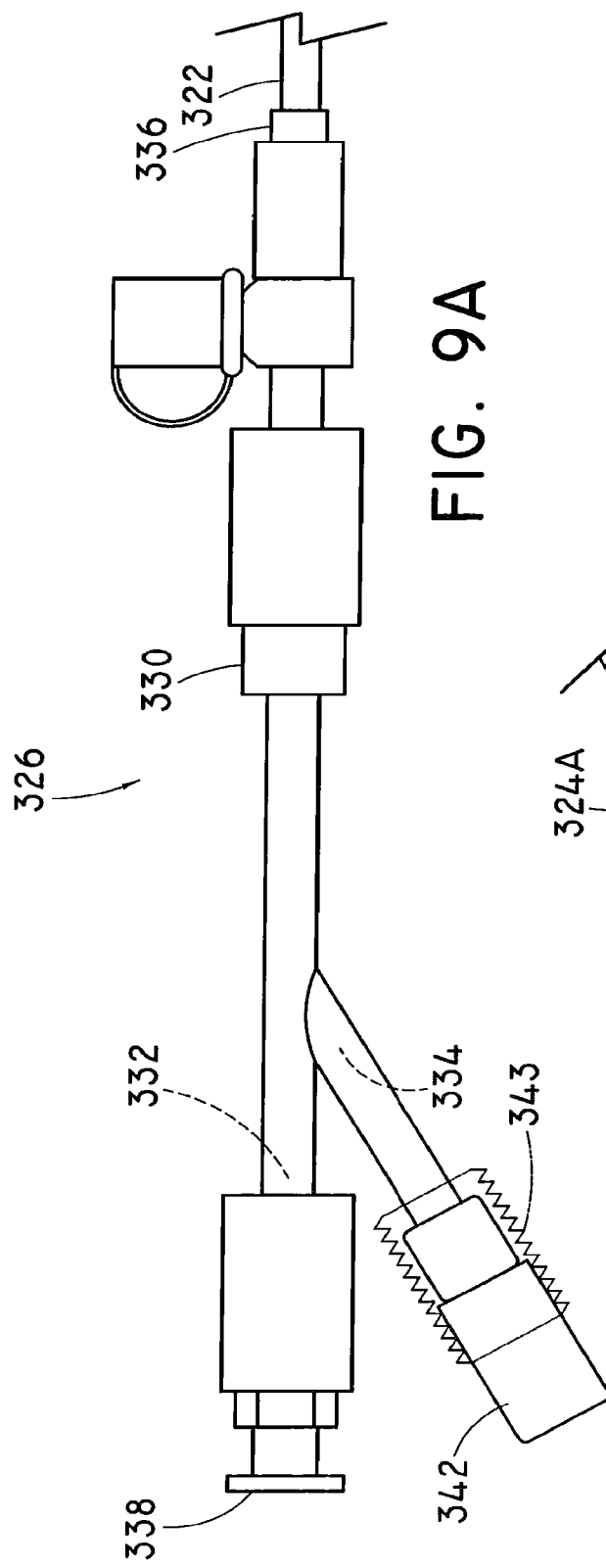
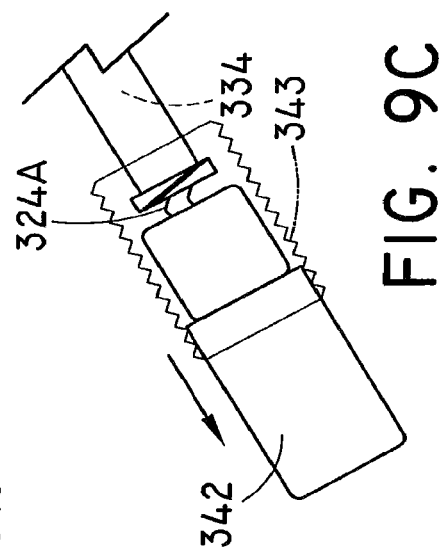
FIG. 9A
FIG. 9C

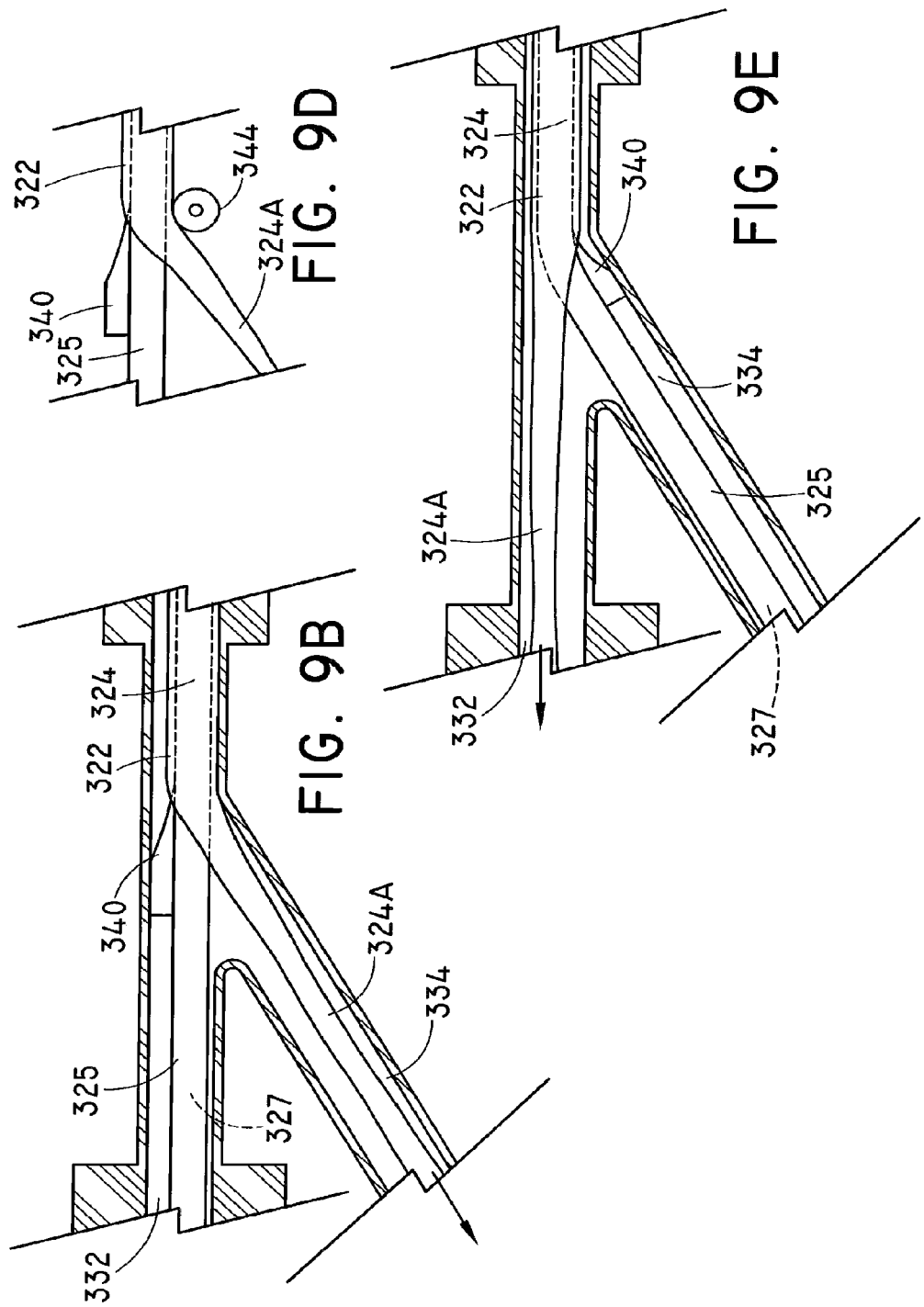

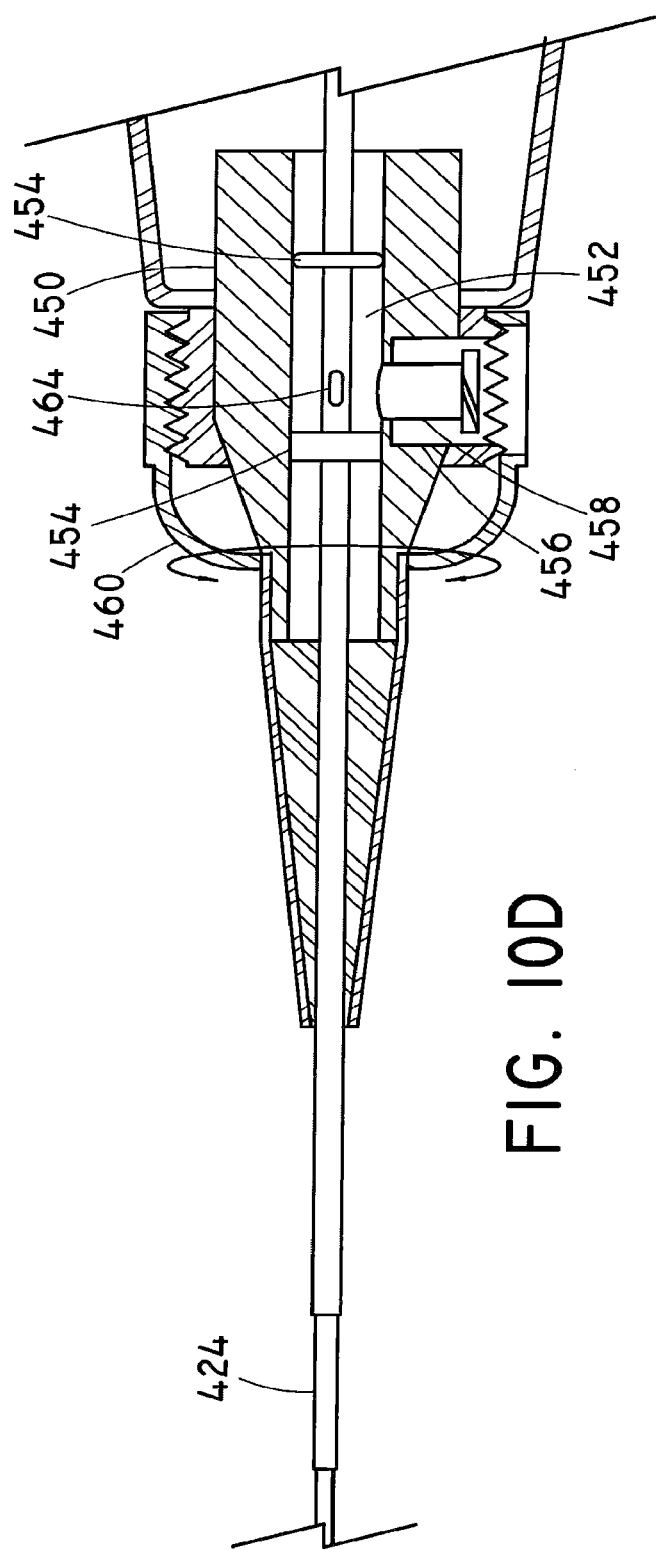

EVERTING DEPLOYMENT SYSTEM AND HANDLE

This application claims the benefit under 35 U.S.C. §121 as a division of U.S. patent application Ser. No. 13/264,331, filed Nov. 9, 2011, which is a National Stage of International Application PCT/US2010/30696 filed Apr. 12, 2010, which claims the benefit of the filing date under 35 U.S.C. §119(e) of Provisional U.S. Patent Application Ser. No. 61/169,590, filed Apr. 15, 2009. The entirety of each application is hereby incorporated by reference.

BACKGROUND

1. Field of the Invention

This invention generally relates to a deployment system for deploying a tubular medical device. More particularly, this invention relates to an everting deployment system for tubular medical devices and a handle for receiving and splitting a tubular member, such as a catheter wall.

2. Background of the Invention

Various diseases of blood vessels may cause a stenosis or occlusion, partially or completely, of the lumen of the blood vessel, which can result in a decrease or complete loss of function. The wide spread occlusion of such diseases demands a number of new methods of medical treatment. Prosthetic devices or stents for sustaining a blood vessel lumen typically have a tubular shaped frame which is introduced in the vessel and fixed in the necessary place to sustain the lumen of the body vessel. One such prosthetic device includes a tubular shaped wire frame with a plurality of interconnected cells and flexible interconnections. The device is collapsible and is contained in a tubular sheath for introduction into the body of a patient. When the device is positioned in the occluded region of the body vessel, it is released from the tubular sheath and permitted to expand radially against the wall of the body vessel.

There are many types of introducers. One such type is the push/pull type of introducer. The push/pull type of introducers includes the category of introducers that require pushing the prosthetic device out of the distal end relative to the sheath or pulling the sheath in the proximal direction relative to the prosthetic device. Regardless, these introducers induce sliding interaction forces between the prosthetic device and the sheath.

The sliding interaction forces may be adverse for a number of reasons. One is the sliding interaction forces between the introducer and a drug coated prosthetic device and the sheath may affect the integrity of the coating or may even rub off the coating. Furthermore, the drug coating of the prosthetic device may present a "sticky" surface that result in a greater frictional force that must be overcome when using these introducers. Another reason is the sliding interaction forces between the introducer and a stent with a graft covering or an implantable valve with valve material. In both instances the integrity of the graft or valve material may be affected, including being torn or stressed. Furthermore, longer stents, especially self-expanding stents, present greater frictional forces to overcome when deploying. This is primarily due to the increased area of contact between longer stents and the luminal wall of the introducer. The longer self-expanding stents may also have greater radial expanding forces against the luminal wall of the introducer that also need to be overcome during deployment with these introducers.

Another type of introducer, described in more detail below, may be called a rolling membrane, roll sock, or everted liner introducer. This type of introducer is particularly beneficial to overcome the problems of the push/pull introducer. The everted liner introducer typically has a sheath connected to an inner member disposed within the sheath by an everted liner. The everted liner is folded on itself and can define a stent retaining region where the prosthetic device is loaded. During deployment, the sheath and the inner member move relative to one another to peel the everted liner away from the prosthetic device. At least one advantage of the everted liner introducer is the ability to deploy the prosthetic device without inducing the sliding interaction forces between the prosthetic device and the luminal wall of the introducer. Instead, during deployment the prosthetic device remains relatively stationary while the everted liner is rolled away from the prosthetic device thus substantially eliminating the sliding interaction forces.

One limitation of the everted liner introducer is the amount of length the sheath must be pulled in the proximal direction to deploy the prosthetic device. Because the everted liner is folded on itself, the sheath typically must be pulled back about twice as far as the length of the prosthetic device to deploy the prosthetic device. For example, for a 140 mm prosthetic device, the sheath must be pulled back about 280 mm. This can make the handle very long and cumbersome to operate. As a result, it also becomes difficult for the physician to regulate and maintain the portion of the sheath that is pulled back.

Another limitation can be stent jumping. Stent jumping is primarily the ability of the prosthetic device to jump or move during deployment due to the radial force exerted by a partly exposed prosthetic device acting to pull the unexposed portion from the stent retaining region. Stent jumping can cause the prosthetic device to deploy prematurely, deploy to an unintended location, and/or cause damage to the vessel wall due to the impact of the tubular medical device suddenly exiting the stent retaining region. Flushing air from the stent retaining region and catheter prior to deployment may also be problematic because the inner member is disposed within the lumen of the sheath, leaving very little area for the flushing fluid to travel. Since the everted liner must be rolled on the prosthetic device during loading while maintaining the prosthetic device in the compressed configuration, loading the prosthetic device within the everted liner of the everted liner system can also be problematic.

SUMMARY

Accordingly, a stent deployment system, handle, and method of loading of a medical device are provided. The stent deployment system may be particularly useful for tubular medical devices having longer lengths of about 140 mm or longer. Another example of an application for the stent deployment system is for tubular medical devices that have been coated with a therapeutic agent and/or have a graft material. The stent deployment system may also provide flushing capabilities, and may be adapted to ensure that the tubular medical device does not jump forward during deployment thus providing enhanced accuracy of the stent deployed location.

In one embodiment, the stent deployment system includes an outer catheter having a tubular wall defining a lumen disposed about a longitudinal axis between a proximal end and a distal end. The tubular wall of the outer catheter includes an outer sheath, an inner liner and a structural layer bonded therebetween. The inner liner has a portion that extends past the distal ends of the outer layer and the structural layer. The structural layer is disposed along the outer catheter, and can include a portion of braid and/or coil along different portions of the outer catheter. It is preferable to have only a coil structure that has a longitudinal distance to surround at least the tubular medical device. The system also includes an inner catheter disposed within the lumen of the outer catheter. The inner catheter has a proximal end and a distal end and defines a lumen. The outer catheter and the inner catheter can be configured and oriented to define an annular lumen. The inner catheter can have a first portion with a first diameter and a second portion with a second diameter that is less than the first diameter thereof to define a stent retaining region between the second portion and the inner liner. The extended portion of the inner liner is inverted to define radial outer and inner portions. The inner portion of the extended portion of the inner liner is attached to the first portion of the inner catheter. Relative movement between the outer catheter and the inner catheter can cause the inversion or eversion of the extended portion of the inner liner.

The inner liner may include a lubricious material to permit sliding interactions more easily between the inner and outer portions of the everted inner liner. The inner liner may also include a low durometer material or a sticky material to enhance the frictional contact between the inner liner and the tubular medical device when loaded and prevent stent jumping. The extended portion of the inner liner may also have a larger diameter more proximal to a portion with a smaller diameter to facilitate inversion of the inner liner. A weakened region can be formed in the tubular wall of the outer catheter, and is particularly useful when splitting the tubular wall. The weakened region can be oriented axially and sized to be at least as long as the tubular medical device. The weakened region may also be defined by a discontinuous structural layer axially along the tubular wall so that it includes only a polymer material. It is preferable to position the weakened region at the proximal end of the outer sheath.

To facilitate flushing, at least one port may be disposed in the side wall of the inner catheter, in communication with the inner catheter lumen. A port and a branch lumen can be interconnected with the lumen and in fluid communication with one another. Optionally, an axial groove can be disposed along the outer surface of the first portion of the inner catheter, wherein one end of the groove is for receiving fluid delivered along the annular lumen, and the other end of the groove is in communication with the stent retaining region.

The system may also include a handle disposed at the proximal end of the outer catheter, configured to permit relative movement between the outer and inner catheters in order to invert or evert the extended portion of the inner liner. The handle may include a splitter configured to slice the wall of the outer catheter axially in a distal direction to form a sliced portion of the outer catheter. The handle may also include a rotatable mechanism attached to the sliced portion of the outer catheter. Rotation of the rotatable mechanism retracts a portion of the outer catheter into the handle and winds the sliced portion of the outer catheter about the rotatable mechanism.

In another embodiment, a handle is provided for a stent deployment system that has a tubular member with a wall defining a lumen about a longitudinal axis between a proximal end and a distal end. The tubular member may be the outer catheter of the stent deployment system described above or another tubular member. The handle includes a housing having a cavity and a port configured to receive the tubular member within the housing cavity. The handle can also include a splitter configured to slice the tubular member axially along the wall thereof in a distal direction to form a sliced portion of the tubular member. The splitter may include a cutting edge to better slice the wall of the tubular member. A guiding member may be provided to guide the tubular member to the splitter. As mentioned previously, the handle may also include a rotatable mechanism attached to the sliced portion of the outer catheter. Rotation of the rotatable mechanism retracts a portion of the outer catheter into the handle and winds the sliced portion of the outer catheter about the rotatable mechanism. Furthermore, the rotatable mechanism can be pre-tensioned, for example with use of spring, with a spring force sufficient to retract the tubular member. This allows easier manipulation of the outer sheath during retraction, especially for longer stents when the outer sheath due to the required length of retraction can be unmanageable or more difficult. A control mechanism, as well as a switch and/or a rotational speed controller, can be coupled to the rotatable mechanism in order to regulate the rotation thereof. Various configurations of pull handles are provided to quicken the retraction of the outer catheter.

Yet, in another embodiment, a method of loading a tubular medical device within a stent deployment system is also provided. The method can include one or more steps of loading the tubular medical device in the compressed configuration within a lumen of a tubular sleeve, with the tubular sleeve sized to receive the tubular medical device; abutting the stent retaining region of the stent deployment system against a first end of the tubular sleeve; tearing the tubular sleeve from the first end to translate the tubular medical device toward the stent retaining region such that a portion of the tubular medical device is inserted in the stent retaining region; and inverting the inner liner by relative movement between the outer catheter and the inner catheter to receive and load the tubular medical device within the stent retaining region of the stent deployment system.

The above, as well as other advantages of the present invention, will become readily apparent to those skilled in the art from the following detailed description of a preferred embodiment when considered in the light of the accompanying drawings.

BRIEF DESCRIPTION OF THE DRAWINGS

FIGS. 3A-3C are side views depicting a method of manufacturing a stent deployment system.

FIGS. 4A-4C are side views depicting a method of manufacturing an outer sheath of a stent deployment system.

FIG. 4D is a close up view depicting attachment of a rolling liner to an inner catheter.

FIG. 4E is a close up view depicting multiple layers of the outer sheath in FIG. 4C.

FIGS. 6B-6E are a perspective view of a distal portion of one embodiment a stent deployment system.

FIG. 9A is a side view of another embodiment of a handle of a stent deployment system.

FIG. 9B is a cross-sectional view partially illustrating a cutting edge arrangement of the handle in FIG. 9A.

FIG. 9C is a detailed view depicting a withdrawal of a pull handle of the handle in FIG. 9A.

FIG. 9D is a detailed view depicting a guiding wheel of the handle in FIG. 9A.

FIG. 9E is a cross-sectional view partially illustrating an alternative cutting edge arrangement of the handle in FIG. 9A.

FIG. 10D is a top view of a portion of the handle in FIG. 10A, depicting the flushing components.

DESCRIPTION OF PREFERRED EMBODIMENTS

Figure 1A:
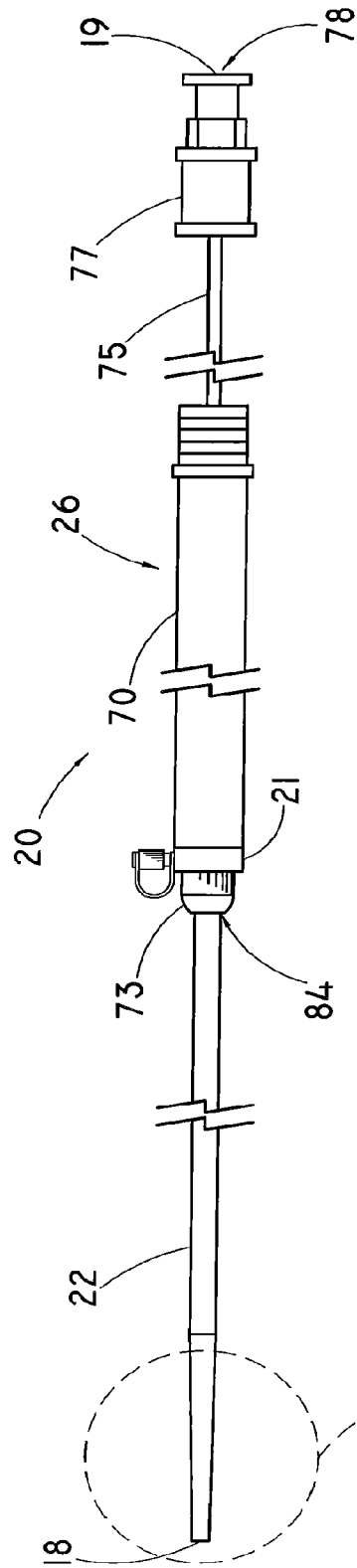
FIG. 1A is a side view of a stent deployment system.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive apparatus, as well as the axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component thereof) that is initially inserted into the patient, or that is closest to the patient during use.

Figure 1B:
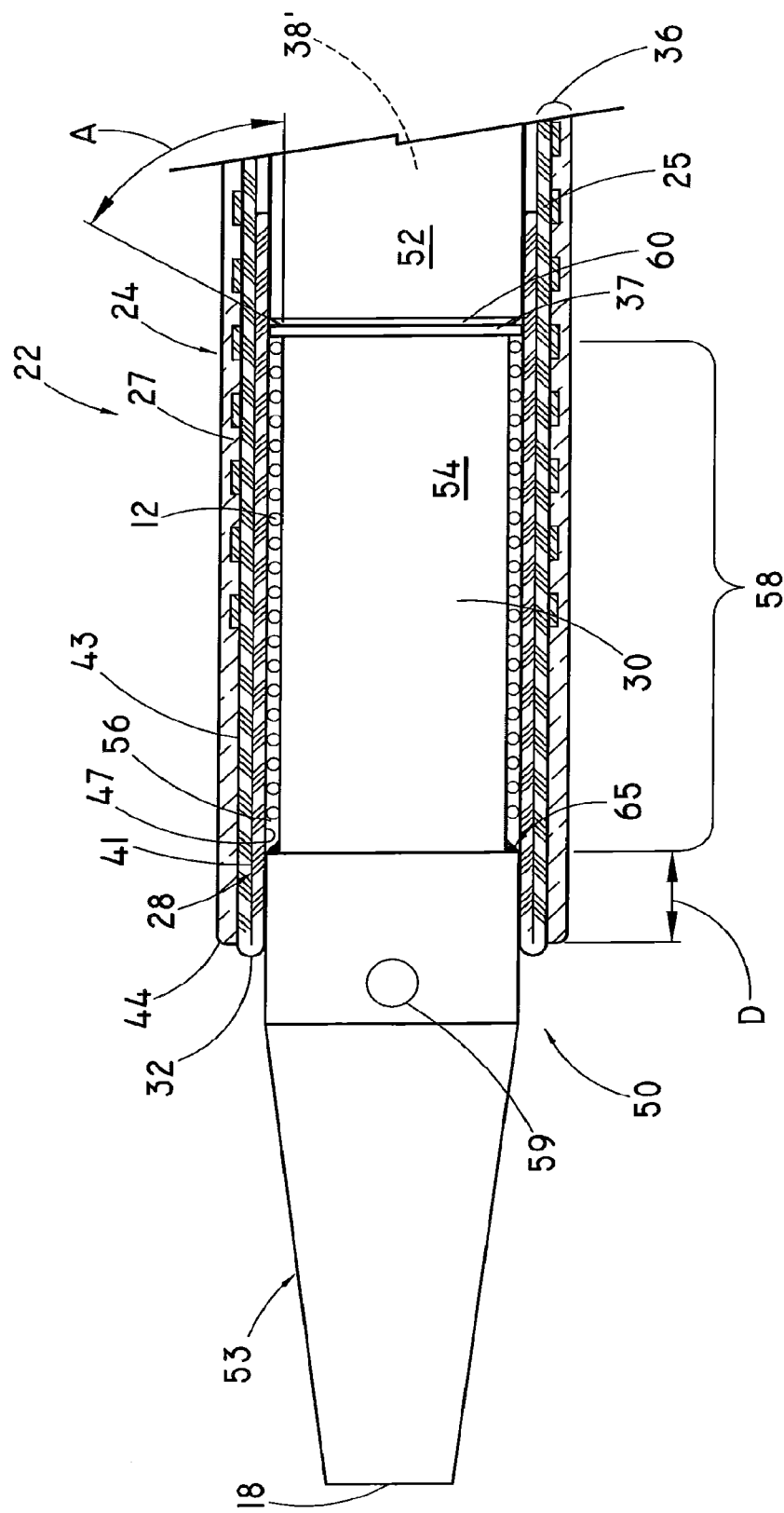
FIG. 1B is a detailed view of a distal portion of the stent deployment system of FIG. 1A.

FIGS. 1A and 1B illustrate one embodiment of a stent deployment system 20. The stent deployment system 20 can be used for delivering a tubular medical device 12 to a target site within a body passageway, such as a body vessel. The tubular medical device 12 is preferably at least partially self-expanding or has self-expanding characteristics. As used herein the term "self-expanding" refers to the tendency of the tubular medical device to return to a predetermined diameter when unrestrained from the catheter, and is capable of moving between a compressed configuration to an expanded configuration. The tubular medical device 12 may be at least partially constructed from one or more of the following shape memory materials: nitinol, shape-memory polymer(s), etc., but may include other material or materials as well. In some embodiments the stent includes one or more areas, bands, coatings, members, or the like that can be detectable by imaging modalities such as X-Ray, MRI or ultrasound. In some embodiments at least a portion of the tubular medical device 12 is at least partially radiopaque. The tubular medical device 12 may also include valves for the arterial or venous applications.

Figure 2:
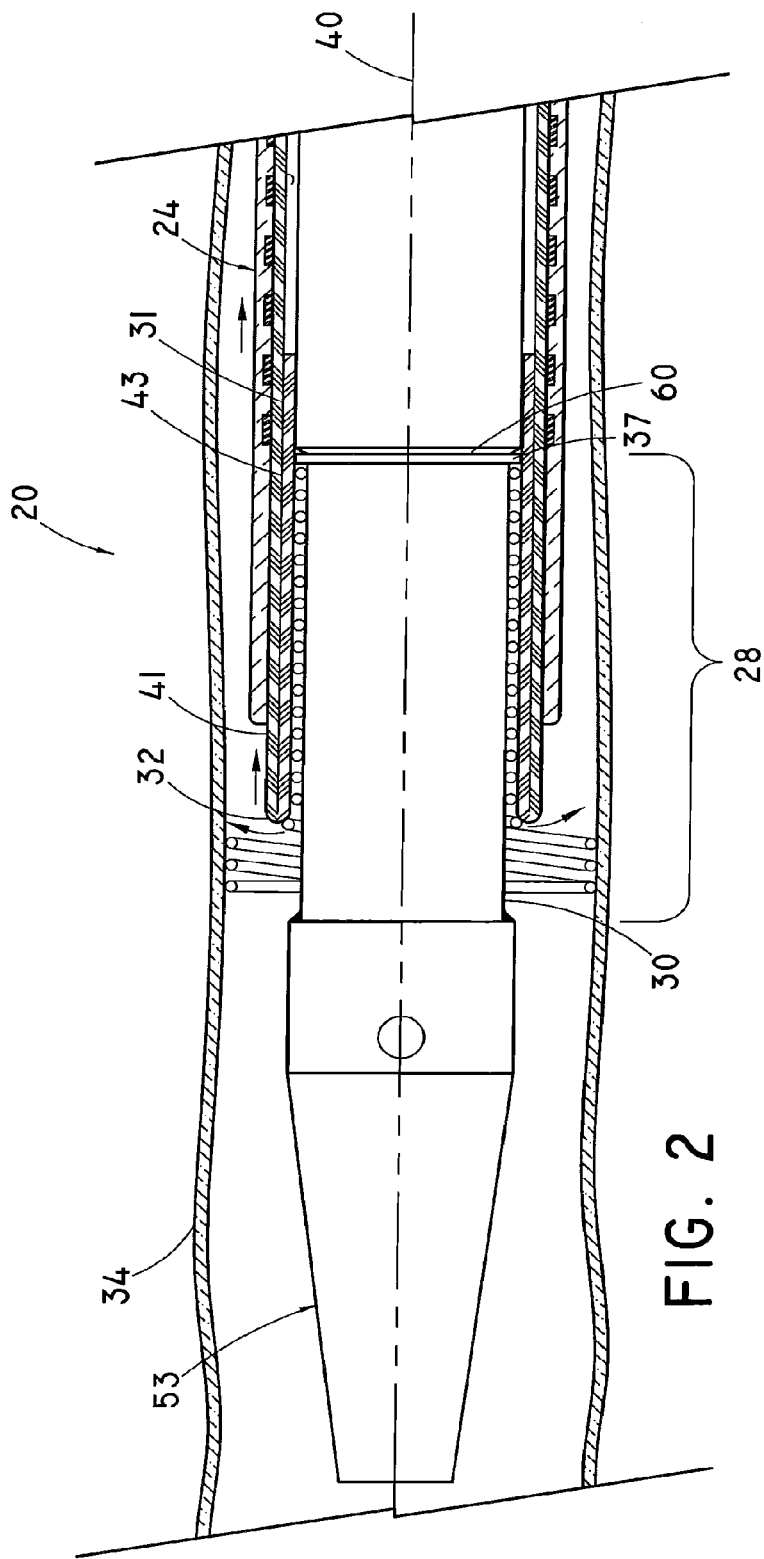
FIG. 2 is a detailed view of the distal portion of the stent deployment system of FIG. 1A within a body vessel, depicting deployment of a tubular medical device.

The tubular medical device 12 may include grafts made of porous fabrics, including but not limited to, PET (polyethylene terephthalate), ePTFE (expanded polytetrafluoroethylene), coated with a therapeutic agent and/or THORALON® biomaterial or other suitable polyurethanes, that can prevent leakage of fluid through the pores of the graft. Polyurethane coated textiles can improve impermeability (i.e., are less prone to allow leakage of fluids, such as serum or water, through the body of the graft, both long and short term). THORALON® biomaterial is a polyetherurethane urea blended with a siloxane containing surface modifying additive, and has been demonstrated to provide effective sealing of textile grafts. THORALON® biomaterial can be obtained from Thoratec Corporation, Pleasanton, Calif. Polyurethanes possess a number of desirable properties such as biostability, compliance, biocompatibility, blood compatibility and strength, which are important in many vascular applications. Accordingly, coated textiles provide improved blood compatibility, as well as strong and compliant reinforcement or replacement of the diseased area. Coatings may also provide a non-thrombogenic and an improved blood compatible lumen surface, in addition to a drug delivery vehicle (e.g., deliver a therapeutic agent) and as a surface-modifying coating to alter mechanical properties such as compliance and wear resistance. Also, THORALON® biomaterial may be applied as a foam to promote cell adhesion (such as endothelial cells) and to form a neointima in all vascular graft applications According to FIG. 1A, the stent deployment system 20 has a distal end 18 and a proximal end 19 and generally includes a catheter body 22 and a handle 26 proximate the proximal end 19 of the stent deployment system 20. With reference to FIG. 1B, the catheter body 22 is constructed of multiple catheters or sheaths, namely an outer sheath 24 and an inner catheter 30 having a rolling liner 32 disposed therebetween, as described later. A portion of the catheter body 22 includes a rolling membrane region 28. The rolling membrane region 28 includes the rolling liner 32 which can be everted or inverted between a fully extended or everted or unrolled position and a fully inverted or folded position, where the axial end of the rolling liner 32 is inverted or rolled within itself. FIG. 1B shows the distal region of the stent deployment system 20, and in particular, FIG. 2 depicts the distal region of the stent deployment system 20, including the rolling membrane region 28, deployed in a body vessel 34.

The outer sheath 24 includes a tubular wall 36 defining a lumen 38 disposed about a longitudinal axis 40 between a proximal end 42 (FIG. 4) and a distal end 44, as shown in FIG. 3A. The outer sheath 24 may be configured to have sufficient hoop strength to retain the tubular medical device 12 in the compressed or pre-delivery configuration. Accordingly, the outer sheath 24 may be constructed from one or more of the materials including but not limited to: various formulations of polyurethane, PTFE (including ePTFE and siliconized PTFE), high density polyethylene (HDPE), polyamide, polyimide, or the like.

The outer sheath 24 may be monolayer or, preferably, has a multi-layer construction. For example, the wall 36 of outer sheath 24 can include an outer layer, a structural layer and an inner layer. The outer layer 27 may be constructed of the material described above in relation to the outer sheath. Preferably, the outer layer 27 is made of a heat formable polyamide material, such as nylon, a polyether block amide (PEBA), polyurethane or the like. The inner layer is preferably the rolling liner 32 as further described below.

According to FIG. 3A, the rolling liner 32 includes a wall having an outer surface 31 and a luminal surface 33 defining a lumen 35 disposed about the longitudinal axis 40 between a proximal end and a distal end 39. Hereinafter, the reference numeral 38' will be designated to define the passageway of the outer sheath 24 with the attached rolling liner 32. The distal end 39 of the rolling liner 32 can extend past the distal end 44 of the outer sheath 24, where such region 86 extending past can be inverted to define the rolling membrane region 28, which changes length as the rolling liner 32 is inverting or everting. The rolling liner 32 can be everted or inverted between a fully extended or everted or unrolled position (FIG. 3A) and a fully inverted or folded position (FIG. 1B), where the distal end 39 of the rolling liner 32 is inverted or rolled within itself.

As illustrated in FIG. 2, relative movement between the outer sheath 24 and the inner catheter 30 urges the rolling liner 32 to evert or invert and slide against itself (between the inner surface of the outer portion 41 and the outer surface of the inner portion 43 of the rolling liner 32. When the outer sheath 24 is retracted in the proximal direction, the inner surface of the inner portion 43 is pulled back off (or peeled off) of the tubular medical device 12, allowing a portion of the tubular medical device 12 to move or expand between the compressed configuration to the expanded configuration. The outer sheath 24 continues to be pulled back to further peel the inner surface of the inner portion 43 off until the entire tubular medical device 12 is fully expanded and deployed into the body vessel 34. The rolling action of the rolling liner 32, such as is depicted during retraction of the outer sheath 24 in FIG. 2, can reduce and/or eliminate the sliding interaction between the outer sheath 24 and the tubular medical device 12. The rolling action also substantially prevents the tubular medical device 12 from sliding or moving longitudinally as the rolling liner 32 is peeled away, which permits immediate expansion of the tubular medical device 12 and engagement with the wall of the vessel.

Preferably, the rolling liner 32 comprises a lubricious material, and more preferably, a fluoropolymer. Most preferably, the fluoropolymer comprises polytetrafluoroethylene (PTFE). The rolling liner 32 can have a uniform inside diameter ranging up to about 30 French (10 mm), or even higher in some instances. The wall thickness of the rolling liner 32 will typically range between about 0.001 and 0.003 inch (0.0254 and 0.076 mm), and is preferably about 0.0015 inch (0.038 mm). Even larger, or smaller, wall thicknesses may be appropriate in a particular case. Those skilled in the art will appreciate that all dimensions recited herein are exemplary only, and that the apparatus described herein may be constructed to be of any size necessary and appropriate to accomplish the purposes for which the sheath is to be employed. Preferably, the rolling liner 32 is uniform the entire length of the passageway 38' of the outer sheath 24, thereby allowing passage of the largest possible diameter tubular medical device 12 therethrough. The lubricious material of the rolling liner 32 presents a slippery luminal surface 33 to allow easy insertion and withdrawal of the tubular medical device 12. The wall of the rolling liner 32 can have sufficient radial rigidity to prevent the turns of braid and coil of a structural layer 25 from protruding into passageway 38'.

PTFE is the preferred material for the rolling liner 32. PTFE is configured to provide suitably high longitudinal tensile strength which permits the rolling liner 32 to be longitudinally rolled and unrolled with higher forces, and a sufficient transverse tensile strength to retain the tubular medical device 12 in the compressed configuration. PTFE also provides structural integrity and durability at a lower thickness up to 0.002 inches to be repeatedly rolled over and unrolled from the tubular medical device 12, and to sustain accidental nicks and breaks.

Figure 4:
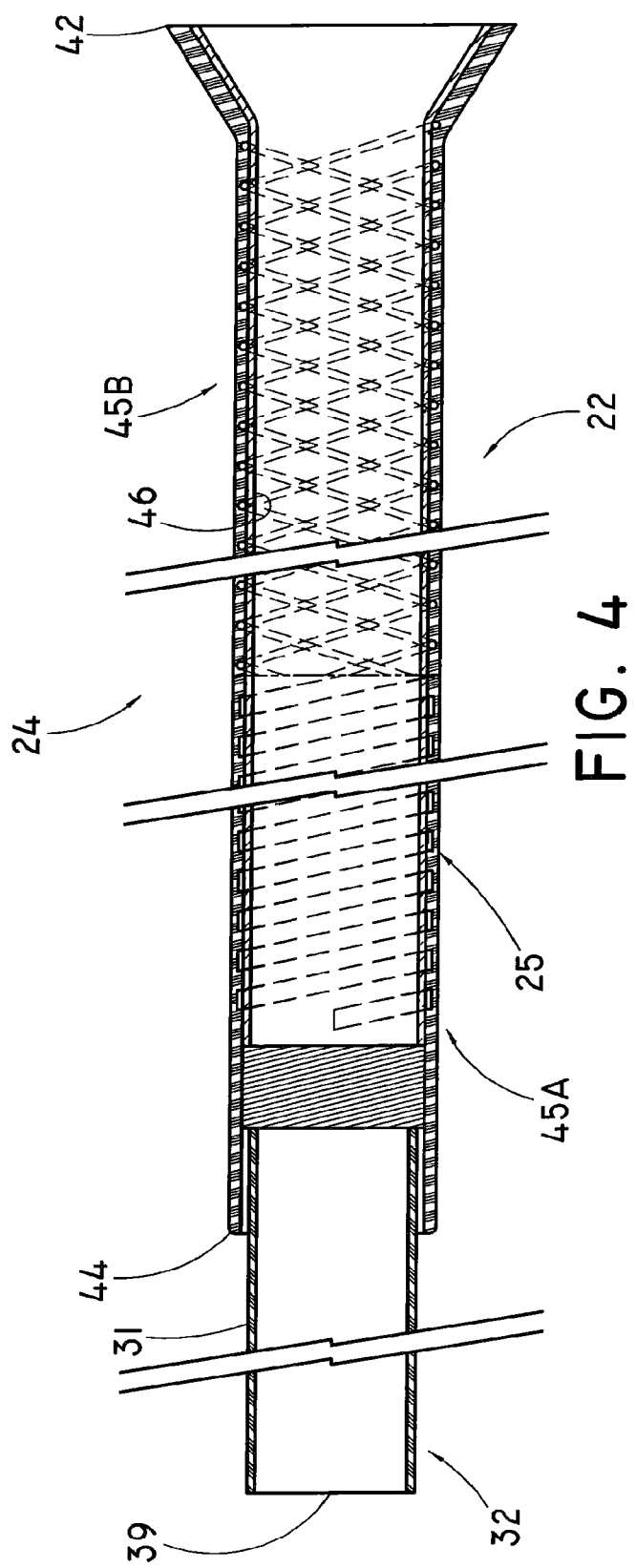
FIG. 4 is a side view of a stent deployment system depicting various structural layers of an outer sheath.

With reference to FIGS. 1B and 4, the structural layer 25 can include a medical grade polymer or metal braid and/or coil. The braid comprises a plurality of crossed wires or filaments that may vary in number, and pitches. Braids are well-known reinforcements for medical devices, and those skilled in the art are well aware of suitable techniques for applying a braided structure to a tubular member for medical applications. The braid typically can provide better bi-directional translation of torque along the outer sheath. The coil may include a flat wire or the like. The coil typically provides better kink resistance. As with braids, coils are also well-known reinforcements for medical devices, and those skilled in the art are well aware of suitable techniques for applying a coil to a tubular member for medical applications. One example of a catheter body construction is the FLEXOR sheath or other sheaths of Cook, Incorporated, Bloomington, Ind., for example, U.S. Pat. No. 5,380,304 to Parker and issued on Jan. 10, 1995, incorporated by reference herein, U.S. Patent Publ. No. 2006/0200110A1 to Lentz et al., incorporated by reference herein, and U.S. Patent Publ. No. 2010/0049168A1 to Parker et al., incorporated by reference herein. A portion of the outer sheath 24 can have one pattern of braid or coil, while another portion can have the same or a different pattern of braid or coil. For example in FIG. 4, a distal region 45A that includes about 10-50% of the length of the outer sheath 24, can have a coil pattern. The other regions 45B of the outer sheath 24 may have the braid for about 50-90% of the length. Preferably, the distal region 45A is sized to have a length that at least coincides with the length of the loaded tubular medical 12.

Preferably, the luminal surface of the outer layer 27 is entirely lined with the rolling liner 32. This can permit the catheter body 22 to have a lower profile because the thickness due to adding another layer of a rolling member is removed. The catheter body 22 can also be constructed in fewer steps as a separate bond between the rolling member and the outer sheath is unnecessary. The outer layer 27 can connect to the outer surface 31 of the rolling liner 32 through the spacings of respective filaments of the braid, or through the turns of the coil, of the structural layer 25. The heat formable material of the outer layer 27 melts upon heating, such that portions flow between the respective filaments or turns of the braid or the coil, and bond to the outer surface 31 of the rolling liner 32 to form the outer sheath 24. In another embodiment, a portion of the outer surface 31 of the rolling liner 32 can serve as a lining and attach to a portion of a luminal surface 46 of the outer sheath 24.

Referring to the FIG. 1B, the inner catheter 30 is shown disposed within the passageway 38'. The inner catheter 30 has a proximal end 48 (FIG. 1A) and a distal end 50, and may have at least a portion extending past the proximal end of the tubular medical device 12. Preferably, the inner catheter has a first portion 52 having a diameter and a second portion 54 distal to the first portion 52, having a diameter being less than the diameter of the first portion 52. The second portion 54 can extend past the proximal and/or the distal end of the tubular medical device 12. The inner catheter 30 may also have a third portion distal to the second portion 54, having a diameter being less than the diameter of the second portion 54. The inner catheter 30 can be made of any suitable material such as PEEK, polyvinyl chloride (PVC), polyimide, polyimide reinforced with a stainless steel braid, polyurethane, nylon, metal tubing such as nitinol or stainless steel, and the like. The inner catheter 30 may also be formed as a coil or a solid-core wire guide. In one embodiment, the proximal portion of the inner catheter 30 is formed from nylon tubing while the distal portion, and especially the portion where the tubular medical device is loaded, is formed from polyimide so as to provide the proximal and distal portions with different physical properties such as varying stiffness or flexibility.

In FIG. 1B, a transition 60 is defined between the first and second portions 52, 54 of the inner catheter 30 to decrease stress risers. Though the transition 60 shown in the Figures is tapered at approximately 60°, the transition can be tapered at an angle A between about 20° to about 90° relative to the longitudinal axis. The transition 60 can function as a seat or rest for the loaded tubular medical device 12, with the transition 60 abutting (or at least adjacent to) the proximal end of the tubular medical device 12. However, the tubular medical device can ride along the tapered transition 60 thereby potentially causing stent jumping when deploying and/or deformation in the tubular medical device. With reference to FIG. 1B, in order to prevent this, a ring 37 of material, such as stainless steel or other biocompatible metal or vinyl radiopaque tubing (VRT) or other biocompatible plastics, may be attached or coupled to the tapered transition 60 to mechanically block the loaded tubular medical device from riding up the transition 60. The ring 37 may have a cylindrical lumen or may be a lumen similarly shaped to match the degree of taper of the transition. The ring 37 has an outer diameter or cross-sectional area that is less than luminal diameter of the outer sheath 24. The ring 37 may also be sized to cover a portion or all of the transition 60 and may even extend to a portion surrounding the second portion 54 of the inner catheter 30.

A distal tip 53 can be attached to the distal end 50 of the inner catheter 30. Generally, the distal tip 53 includes a cavity, where the second portion 54 (or third portion) of the inner catheter 30 is inserted therein. An adhesive, such as cyanoacrylate or the like, can be applied through a port 59 to bond the distal tip 53 to a portion of the inner catheter 30. A bead 65 of material, such as an adhesive or polymer, can be applied to the edge of the distal tip and tapered to smooth the transition and/or reduce the sharpness between the edge and the inner catheter. Alternatively, the proximal end of the distal tip may be tapered to the diameter of the inner catheter. A portion of the distal tip 53 may be retracted into an annular space 56 at a distance D, such as about 2 mm, inside from the distal end 44 of the outer sheath 24. The distance D should be sufficiently sized to provide a smooth transition between the distal tip 53 and the outer sheath 24 and to lessen the chance of kinking directly behind or just proximal of the distal tip 53. Referring to FIG. 3C, the inner catheter 30 can include a guide wire lumen 57 through the center thereof and along the longitudinal axis 40 where a guide wire can be inserted therein.

An annular space 56 is created between the inner surface 47 of the inner portion 43 of the rolling liner 32, when folded back on itself, and the second portion 54 of the inner catheter 30 to define a stent retaining region 58, as shown in FIG. 1B. That is, an inner circumferential boundary of the annular space 56 is defined by the second portion 54 of the inner catheter 30, an outer circumferential boundary is defined by the inner surface 47, and a proximal boundary is defined by the transition 60 between the first and second portions 52, 54 of the inner catheter 30. In the present embodiment, when the tubular medical device 12 is disposed about the stent retaining region 58, the tubular medical device 12 is restrained in a reduced diameter or pre-delivery configuration by the retractable outer sheath 24 and/or the rolling liner 32, which are disposed about the entire length of the tubular medical device 12 prior to delivery.

FIGS. 3A-3C illustrate a method of assembling of the catheter body 22 of the stent deployment system 20. In FIG. 3C, a portion of the outer surface 31 of the rolling liner 32 is disposed between a first attachment point 61 along the luminal surface of the outer layer 27 and a second attachment point 62 along a portion of the inner catheter 30. The first attachment point 61 can be a bond created between the rolling liner 32 and the outer layer 27, as described above. In FIG. 3A, a portion 86 of the rolling liner 32 that extends past the distal end 44 of the outer sheath 24 is fully extended or unrolled. According to FIG. 3B, the distal end 39 of the rolling liner 32 is then partially inverted into the passageway 38' to form the outer and inner portions 41, 43 at a certain length. The certain length of inner portion 43 may be primed for bonding by etching, roughening or other like means, before being inverted. In FIG. 3C, the inner catheter 30 can be inserted in the distal end of the inverted rolling liner 32 and attached as described below to create the second attachment point 62. The inner catheter 30 can be further retracted in outer sheath 24 to create the stent retaining region 58 in order to receive the tubular medical device.

To attach the inner catheter 30 with the outer sheath 24, the inner catheter 30 is inserted into the end of the outer sheath 24 and the end 39 of the extended rolling liner 32 is aligned with the distal end of the first portion 52 of the inner catheter 30. Before alignment, an adhesive may be added along the second attachment point 62 or contact region of the rolling liner 32 and the inner catheter 30. Preferably, the adhesive is applied to less than half the circumference so that not to fill all of the ports or grooves, if included in the inner catheter 30. Heat shrink tubing may then be coaxially disposed about the positioned rolling liner 32. Preferably, a portion of the rolling liner 32 may be inverted or rolled inward for about 1 cm or more and the fold of the rolling liner 32 may be aligned with the end of the first portion 52 of the inner catheter 30 or located proximal to the end as shown in FIG. 3C. In this instance, heat shrink tubing, about 2 cm or more, may then be coaxially positioned around a portion of the inner catheter 30 and inserted between the inverted liner 32. Optionally, the heat shrink tubing can be coaxially disposed around the outside portion of the inverted liner and not inserted between the inverted liner 32.

Heat can be applied to bond the rolling liner 32 to the inner catheter 30. Optionally, the proximal end of the heat shrink tubing can be grinded and/or, an adhesive, such as a UV curable adhesive, may be provided to smooth out or taper the transition down from the heat shrink tubing to the diameter or cross-sectional area of the rolling liner 32. This can permit easier movement of the inner catheter within the outer sheath. After attachment, the inner catheter 30 may be moved inward relative to the outer sheath 24 to invert the rolling liner 32. With the attached rolling liner 32, the tubular medical device can be inserted into the stent retaining region 58 by inverting the liner 32 onto the tubular medical device.

In a preferred embodiment, according to FIG. 4A, the distal portion 45A of the outer sheath 24 includes a structural layer 25A, preferably a coil structural layer. The longitudinal length of the structural layer 25A is sized to be at least the size of the tubular medical device. The distal portion 45A is formed by placing an inner liner 32A, preferably PTFE liner, on a mandrel. The material forming the inner liner 32A may be further heat treated or reinforced with fibers to strengthen the liner in order to prevent the liner from easily tearing longitudinally during the rolling function. A portion 86 of the inner liner 32A is sized to extend past a distal end 44' of an outer layer 27A, preferably a polyether block amide, nylon, polyurethane or the like, to form the rolling liner aspect of the stent deployment system 20. The exterior of the inner liner 32A can be etched or roughened, as described herein, for better bonding to the coil structural layer 25A and the outer layer 27A. A portion of the interior of the inner liner 32A, for example about 3 cm, can also etched or roughened for better bonding to the proximal portion 45B of the outer sheath 24. The outer surface of the distal portion of the extended portion 86, about 2 cm from the end 39, as well as the interior surface of the lumen, about 3 mm from the end 39, may also be etched or roughened. After the inner liner 32A is sized and placed on the mandrel, the coil structural layer 25A is coaxially disposed to surround the inner liner 32A. Next, the outer layer 27A is also coaxially disposed to surround the coil structural layer 25A and the inner liner 32A to form the layers of the distal portion 45A. A heat shrink liner (not shown) can be coaxially placed around the layers, and then heat can be applied to bond the layers one to another to form the distal portion 45A of the outer sheath 24.

Furthermore, the extended portion 86 of the inner liner 32A may have a change in outer diameter, such as stepped portion or tapered portion, in order to facilitate the everting function, as well as the bonding to the inner catheter. FIG. 4A shows the extended portion 86 having two stepped portions 86A, 86B of different outer diameters. One method of forming the change in diameter is to insert a mandrel shaped for the intended change in outer diameter into the lumen of the distal portion 45A. For example, a stepped mandrel can be inserted having a first diameter corresponding to a portion of the inner liner that is sized to be about the size of the lumen of the distal portion 45A and a second diameter, smaller than the first diameter, corresponding to another portion of the inner liner distal to the other portion that is sized to be about the same size as the first portion 52 of the inner catheter 30. Preferably, the second diameter is sized to be slightly smaller than the first portion 52, about 0.003 to 0.004 inches, for snugly fitting thereover. The stepped mandrel is inserted into the lumen of the distal portion 45A and the step of the stepped mandrel is positioned along the extended portion 86 of the inner liner. Preferably the step of the stepped mandrel is placed to form a step 87 in the extended portion 86 at least the length of the tubular medical device from the distal end 44' of the outer liner 24A, or about the length of the tubular medical device in addition to 3-7 mm. Heat from a heat source, such as a heat gun, is applied to the extended portion 86 for a period of time to soften the liner material, after which the distal end 39 of the distal portion 45A is pulled to conform the extended portion 86 to the shape of the stepped mandrel. This also stretches the extended portion by a few centimeters. The assembly is permitted to cool and the extended portion 86 now has a step 87 from the stepped shape of the mandrel.

FIG. 4B illustrates a preferred embodiment of the proximal portion 45B of the outer sheath 24, which includes a structural layer 25B, preferably at least a braided structural layer. Similarly to the manufacturing of the distal portion 45A described above, the proximal portion 45B is formed first by placing a second inner liner 32B, preferably PTFE liner, on a mandrel. The exterior of the inner liner 32B may be roughened, as described herein, for better bonding to the structural layer 25B and the second outer layer 27B, preferably a polyether block amide, nylon, polyurethane or the like. After the inner liner 32A is sized and placed on the mandrel, the structural layer 25B is coaxially disposed along the inner liner 32B. Next, the outer layer 27B is also coaxially disposed to surround a portion, preferably significant portion, of the structural layer 25B and the inner liner 32B. The outer layer 27B is sized to have an outer diameter larger than the inner luminal diameter of the distal portion 45A. A thinner outer layer portion 27C, preferably a polyether block amide, nylon, polyurethane or the like, is then coaxially disposed at a section 47 toward the distal end of the proximal portion 45B, as shown in FIG. 4B. The thinner outer layer 27C is sized to have an outer diameter that is slightly smaller than the inner luminal diameter of the distal portion 45A, such that the thinner section can fit within the lumen of the distal portion 45A. The length of the section 47, about 3 cm, is sufficient to ensure a strong bond between the portions 45A, 45B. A slight tapered transition 49 can be formed between the thicker and thinner outer layers 27B, 27C to reduce stresses and to abut against the proximal end of the distal portion 45A. The layers of the proximal portion 45B preferably are substantially identical in length, within ordinary manufacturing tolerances. A heat shrink liner (not shown) can be coaxially placed around the layers, and then heat can be applied to bond the layers one to another to form the proximal portion 45B of the outer sheath 24. The distal end 51 of the proximal portion 45B may be tapered to ease insertion into the distal portion 45A. Before insertion, an adhesive, such as Loctite, may be added to the thinner section 47 for better bonding to the distal portion 45A.

FIG. 4C illustrates the assembled distal and proximal portions 45A, 45B of the outer sheath 24. The proximal portion 45B is inserted into the lumen of the distal portion 45A and held in fixed relation to one another to allow the bonding of the adhesive to form the outer sheath 24. A small sleeve 88 of outer liner material, about 1 cm, can be provided around the proximal portion 45B to contact the proximal end of the distal portion 45A. The sleeve 88 can provide a smoother transition from the distal portion 45A to the proximal portion 45B and strain relief. Optionally, another layer 81, such as heat shrinkable liner, can be added at the juncture of the distal and proximal portions 45A, 45B to ensure better bonding between the two. Heat or UV light can then be applied to bond the layers to form the outer sheath 24. It was found that overlapping the structural layers of portions 45A, 45B can inhibit the end of the braided layer from extending radially outward through the wall of outer sheath. FIG. 4E shows a close up view of the various layers of the outer sheath shown in FIG. 4C.

FIG. 4D shows another way of attaching the rolling liner to the inner catheter. A groove 90 can be cut into the wall of the first portion 52 of the inner catheter 30. The groove 90 may extend circumferentially around the entire circumference of the second portion of the inner catheter. The groove 90 may be place a few centimeters proximal to the transition 60 at a depth of about 0.003 inches. An adhesive 92, such as a UV curable adhesive like LOCTITE 3011, can be placed into the groove 90. The inner catheter 30 is placed in the passageway 38' of the assembled outer sheath 24 of FIG. 4C and is translated to a position such that the distal end 39 is just distal to the groove 90. For a better bond, it is preferable that the first portion 52 of the inner catheter is slightly larger than the distal region 86B of the extended portion 86 of the rolling liner so that when inserted there is a snug fit. After placement of the inner catheter, a suture (not shown) may be applied along the outside surface of the extended portion of the rolling liner proximate the groove 90 and tightened to ensure pressure circumferentially along the entire surface. UV light may then be used to cure the adhesive 92 to bond the rolling liner to the inner catheter via the groove 90. The surface 94 of the first portion 52 between the groove 90 and the transition 60 may be roughened. Next, the ring 37 is positioned at the transition 60 and an adhesive, such as such as a UV curable adhesive like LOCTITE 3011, is preferably applied to the gap defined between the ring and the surface of the transition and then cured. Another adhesive, a fast acting adhesive like LOCTITE 4061, is applied to the surface 94 and to the surface of the ring 37. The rolling liner 32 is then carefully rolled over the adhesive between the groove and the transition to a position shown by the dashed lines, and then maintained for a period of time sufficient for bonding. A side port 96 used for flushing is then created in the second portion 54 of the inner liner about 1-3 mm from the ring 37.

In alternative embodiments, the rolling liner 32 is not attached to the inner catheter 30. When the rolling liner 32 is inverted and the tubular medical device 12 is loaded, the radially expansion forces of the tubular medical device circumferentially urge against the inner portion 43 of the rolling liner 32. This can fix the inverted rolling liner 32 in position relative to the loaded tubular medical device. Thus, when everting the rolling liner from contact with the tubular medical device, there is sufficient radial force to prevent the rolling liner from premature removal from the loaded tubular stent when being deployed.

Preferably, the entire length of the outer surface 31 may be chemically etched or mechanically roughened. Etching of the outer surface 31 promotes better bonding between the rolling liner 32 and the outer layer 27. In addition, the surface of the inner portion 43 of the outer surface 31 that rolls inward to form the stent retaining region 58 can be similarly etched or roughened to promote frictional contact between the tubular medical device 12 and the rolling liner 32 to prevent stent jumping during deployment. Stent jumping is primarily the ability of the tubular medical device 12 to jump or move during deployment due to the radial force exerted by a partly exposed tubular medical device acting to pull the unexposed portion from the stent retaining region 58. Stent jumping can cause the tubular medical device 12 to deploy prematurely, deploy to an unintended location, and/or cause damage to the vessel wall due to the impact of the tubular medical device suddenly exiting the stent retaining region 58.

Etching of the inner surface of the inner portion 43 of the inverted rolling liner 32 that defines the luminal surface also provides for better attachment of the rolling liner 32 to the inner catheter 30. It also is preferable that the entire length of the luminal surface 33 of the rolling liner 32 proximal to the attachment point of the rolling liner is not chemically etched or mechanically roughened in order to provide smoother and more lubricious surface than the outer surface 31. This promotes sliding between the outer sheath 24 and the inner catheter 30 along the length of the deployment system 20. Preferably, the inner surface of the outer portion 41 of the rolling liner 32 and the outer surface of the inner portion 43 of the rolling liner is also not etched or roughened in order to facilitate sliding therebetween.

In particular, when the rolling liner is PTFE, several techniques can be used for etching PTFE. The use of specially formulated solvents that extract some of the fluorine atoms of a PTFE liner can be used for etching. These types of solvents leave behind a thin, carbon rich surface layer to which adhesives can attach or bond. Another form of etching involves implanting fine particles of silica in the PTFE rolling liner to create a frictional or rough surface to which adhesives can also attach or bond.

Another way to prevent stent jumping may be to add a surface modification to the inner portion 43 of the rolling liner 32 that is exposed to the tubular medical device 12. The surface modification can be configured to promote better interface and/or frictional contact between the tubular medical device 12 and the rolling liner 32. The surface modification can be typically a thin-film, a monolayer, or a multi-layer attached to the inner portion 43 such that the surface modification does not add substantially to the thickness of the rolling liner 32 and reduce the passageway 38'. The inner portion 43 can be primed for the attachment of the surface modification by, for example, chemical primer, plasma treatment, self-assembled monolayers, chemical degradation, such as base hydrolysis, or the like. Following priming, the surface modification can be applied to the sheath.

Figure 5A:
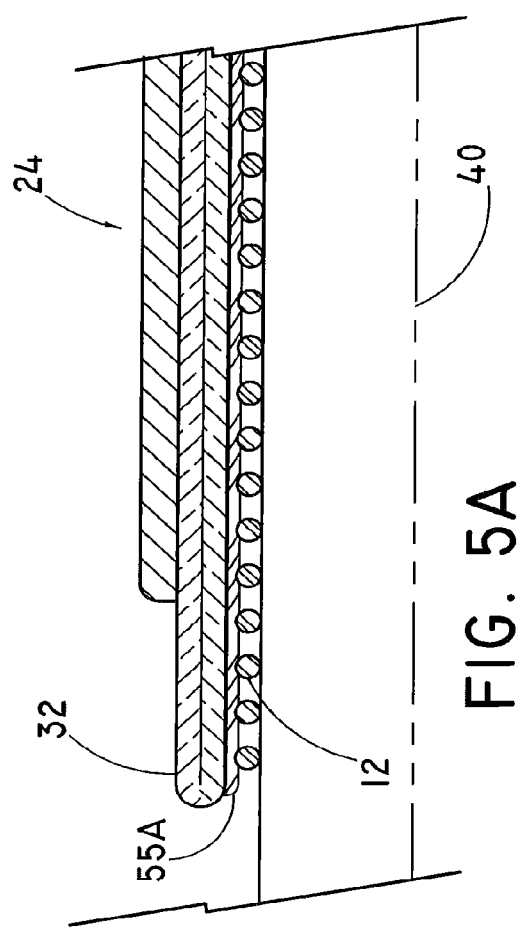
FIGS. 5A-5B are detailed views depicting embodiments of a surface modification to a rolling liner of a stent deployment system.
Figure 5B:
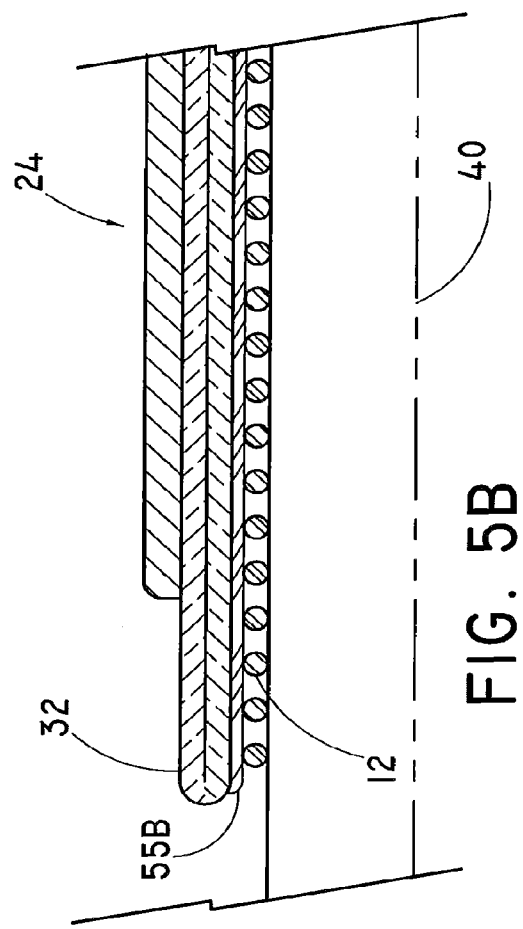

As shown in FIG. 5A, one surface modification can be to add a low durometer material 55A to the inner portion 43 which is configured to promote a portion of the tubular medical device 12 to impinge into the low durometer material 55A, such as urethanes, such as Thoralon, nylons, such as a polyether block amide, and silicones. Low durometer material may also include materials having a durometer of 90 or less (Shore A), such as epoxy, fluoropolymer, polyamide, polycarbonate, polyester, polyethylene, polyolefin, polyurethane, polyvinyl chloride, thermoplastic elastomer, thermoplastic polyurethane, or other materials. Optionally, according to FIG. 5B a sticky or non-lubricious material 55B can be added to the inner portion 43 to increase the frictional contact to the tubular medical device 12. Materials configured to promote interface and frictional contact, such as polyurethanes, silicones, or other materials listed above in connection to the material 55A, may also be used. One preferred surface modification material is polyether (urethane urea), such as BPS-215 component, 23.5% layer, (Thoratec Corporation, Pleasanton, Calif.). BPS-215 is used in THORALON® biomaterial and is a segmented polyether urethane urea containing a soft segment and a hard segment, with the soft segment is made of polytetramethylene oxide (PTMO) and the hard segment is made of 4,4'-diphenylmethane diisocyanate (MDI) and ethylene diamine (ED).

Figure 6A:
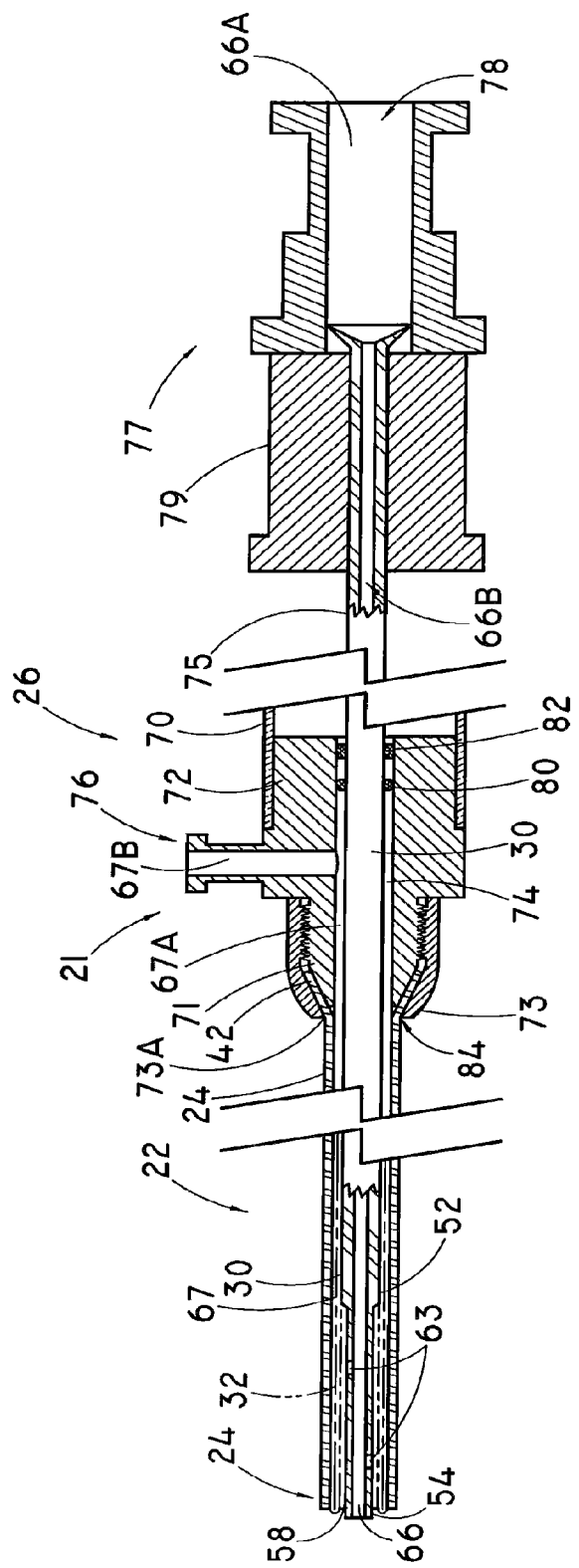
FIG. 6A is a cross-sectional view of a stent deployment system, depicting in more detail one embodiment of a handle.

FIG. 6A illustrates the connection between the catheter body 22 and the handle 26 which includes a hub assembly 21, which can be a check-flow adapter. The hub assembly 21 can include a first attachment end 71 sized to be inserted into a flared proximal end 42 of the outer sheath 24. The first attachment end 71 preferably has ridges or groove for better engagement with the outer sheath 24. A second attachment end 72 disposed at the opposite end of the first attachment end 71 can be sized to be inserted into the end of the cylindrical body 70 of the handle 26. The second attachment end 72 may also be ridged and/or grooved for better engagement with the cylindrical body 70. A cap 73 is provided to sandwich the outer sheath with the first attachment end 71. The cap 73 has a portion 73a sized to receive the catheter body 22 and a second portion 73b sized to receive and engage with the first attachment end 71 of the hub assembly 21. The cap 73 when securably engaged to the first attachment end 71 helps attach the outer sheath 24 of the catheter body 22 to the hub assembly 21 and handle 26. The hub assembly 21 also includes a bore 74 through the body extending from end to the other end. The bore 74 is sized to receive the proximal portion of the inner catheter 30. An annular space 67a defined between the bore 74 and the inner catheter 30 is due to a smaller sized diameter of the inner catheter 30. The hub assembly 21 may also include a fluid delivery port 76. The fluid delivery port 76 includes a lumen 67b in fluid communication with the annular space 67a. Another port 78 for receiving a guide wire can be included at the axial end of the pushrod 75 at a proximal hub assembly 77, which is shown to be connected to a holding bushing 79 that is attached to the pushrod 75. The port 78 can also be used for fluid delivery. The port 78 is in fluid communication with the bore 66a through the hub and a bore 66b through the pushrod, which is in fluid communication with the lumen 66 of the inner catheter 30.

As mentioned before, the fluid delivery port 78 may be used for fluid delivery for flushing and/or drug infusion, while the port 76 can be used only for flushing. The fluid may enter the stent deployment system 20 through the port 76, which is in communication with the lumen 67b and annular space 67a, and in communication with the annular space 67 between the outer sheath 24 and the inner catheter 30. A sealing mechanism 80 can be disposed proximal to the port 76 to sealably engage the outer edge of the inner catheter 30 with the inner edge of the bore 74. The sealing mechanism 80 can substantially prevent any flushing fluid from entering into areas of the handle 26 proximal to the location of the sealing mechanism. FIG. 6A illustrates the sealing mechanism 80 as an O-ring; however, the sealing mechanism can also include a silicone tube, sealant, epoxy or the like. A plastic disc 82 may also be located proximal to the sealing mechanism 80 for additional sealing benefit. The plastic disc may also be used as a gasket seal at the joint between the hub assembly 21 and the cylindrical body 70.

The inner catheter 30 can also include one or more ports 63. Preferably, the port 63 is included on a portion in the stent retaining region 58, for example, the second portion 54 of the inner catheter. This can allow the fluid to disperse inside-out from within the tubular medical device. During the operation of flushing, a plugging or occluding device (not shown) sized and configured to sealably engage the distal end of lumen 66 and/or the port(s) 63 may be inserted at the distal end of the lumen. If the rolling liner 32 is attached to the inner catheter 32, flushing fluid is preferably inserted through port 78. With only the distal end of the lumen 66 plugged, the flushing fluid can exit through the side ports 63, into the stent retaining region 58 and out the distal end of catheter body to flush air out of the stent region. The plugging device can then be removed from sealable contact with the distal end of the lumen 66, and additional flushing fluid can be delivered into the lumen 66 at the port 78 to flush out any more air in the lumen 66. It is appreciated that this method of flushing could be used with other configurations, and related alternative embodiments, shown in FIGS. 6B-6C.

If the rolling liner 32 (shown by dashed lines) is unattached to the inner catheter 30, flushing fluid is preferably inserted through the port 76 and there would be no side ports 63. Flushing fluid can be inserted into the port 76 where the fluid will flow in the annular space 67. In this instance, the fluid can then flow in the gap between the unattached rolling liner and the inner catheter, and into the stent retaining region 58 and out the distal end of the catheter body to flush our air out of the stent region. Fluid can be then delivered into the lumen 66 at the port 78 to flush air out lumen 66. It is appreciated that this method of flushing could be used with other configurations, and related alternative embodiments, shown in FIGS. 6C-6F.

FIG. 6B illustrates a close-up view of the distal portion of the deployment system as described herein. In this embodiment, one or more exit ports 61 can be located at the transition 60 between the first and second portions 52, 54 of the inner catheter 30. The exit ports 61 have branch lumens 69, in communication with the lumen 66. Through the branch lumens 69 and exit ports 61, fluid exits the lumen 66 and enters the stent retaining region 58. In this instance, the flushing fluid will primarily be delivered through the lumen 66.

FIG. 6C is a perspective view of the stent deployment system depicting an alternative embodiment where one or more grooves or channels 57 are located on the outside surface of the first portion 52 of the inner catheter 30. A passage is thus created between the outer sheath 24 and the rolling liner 32 where it contacts the inner catheter and the grooves 57. Fluid may enter the grooves 57 from the outside-in from the annular space 67 to exit the grooves and enter the stent retaining region 58. The grooves 57 preferably extend a certain longitudinal distance past the end of the attached rolling liner, shown as the second attachment point 62, such that sufficient fluid is received for effective flushing.

FIG. 6D is an axial view of the deployment system depicting another embodiment. One or more fluid delivery lumens 68 can be formed in the outer portion of the inner catheter 30. The fluid delivery lumens 68 are connected to exit ports 61 that are disposed at the transition. The fluid delivery lumens 68 can run the entire length of the inner catheter or a partial length. In one aspect, the fluid delivery lumens 68 may be isolated from the lumen 66. Fluid may enter the fluid delivery lumens 68 from the annular space 67 through side ports formed in the first portion 52 of the inner catheter which are connected to the lumens 68 through branch lumens. Optionally, the fluid delivery lumens 68 are in communication with the lumen 66. Here, fluid may enter the fluid delivery lumens 68 from the lumen 66 through branch lumens connecting the lumen 66 with the fluid delivery lumens 68. In both cases, fluid exits the exit ports 61 and enters the stent retaining region.

In another example, such as illustrated in FIG. 6E, one or more side ports 63a, in communication with the fluid delivery lumen 66, may be disposed in the wall of first portion 52 of the inner catheter 30. The side port 63a can be located near the proximal region of inner catheter 30 and/or the transition 60. In one example, a plugging device is inserted in the lumen 66 at the distal end and fluid is injected into the lumen 66 at the proximal end. Because of the pressure difference, fluid will travel via the branch lumens 69 into the annular space 67. In another example, the fluid is introduced directly into the annular space 67 as described above. In both instances, fluid may enter the region between the outer and inner portions of the rolling liner 32 which can lubricate the surfaces to enhance everting or inverting and/or provide a hydraulic pressure to enhance everting or inverting of the rolling liner 32. In addition, one or more ports 61a can be disposed in the inner portion of the rolling liner to permit fluid to enter the stent retaining region 58 outside-in from outside the tubular medical device. Ports 61*a* can be spaced along the circumference of stent retaining region 58, as shown in FIG. 6E. Optionally, the ports 61*a* are disposed only near the transition. Because the distal portion of the rolling liner may need more structural integrity when initially deploying the tubular medical device due to the amount of retraction force used to pull back the outer sheath, fewer holes, if any holes, are needed. The frequency, density, cross-sectional area and/or location of ports can be determined based on the structural integrity of the rolling liner.

Turning to the handle 26 in FIGS. 1A and 6A, a tubular medical device can be deployed using the handle 26, which is disposed proximate the proximal end 19 of the stent deployment system 20. Those skilled in the art will appreciate that various other proximal attachments, such as a hub or a multi-chamber manifold, may alternatively be used to receive the outer sheath 24.

In one embodiment, the handle 26 includes the cylindrical body 70 that is adapted to receive a pushrod 75. The pushrod 75 can axially move between a retracted position where the tubular medical device is in compressed delivery configuration and an inserted position where the tubular medical device is delivered. Between the retracted and inserted positions, the outer sheath 24 can move relative to the inner catheter 30 to cause the rolling liner 32 to evert or invert. The handle 26 may be ready for deployment when the handle 26 is in the retracted position. The user can move the cylindrical body 70 in the proximal direction relative to the pushrod 75 to retract the outer sheath 24 in the proximal direction and evert the rolling liner 32 away from the tubular medical device. The handle 26 includes a port 84 for receiving the catheter body 22 and the port 78, which in this example, is in communication with the fluid delivery lumen 66 of the inner catheter 30 and used for receiving a guide wire. As described above with reference to FIG. 6A, the proximal end 42 of the outer sheath 24 can be flared to engage with the first attachment end 71 of the hub assembly 21. The cap 73 can fit over the catheter body 22 and the flared end 42 engaged with the first attachment end 71 to engage with the hub assembly 21 in a friction fit or secure fashion. This helps fix and seal the outer sheath 24 of the catheter body 22 to the handle 26. The inner catheter 30 can extend longitudinally past the attachment point of the outer sheath 24 in the proximal direction into at least the second attachment end 72. In one example, the inner catheter 30 extends through a portion of the cylindrical body 70 and is attached to the pushrod 75. The lumen 66*b* of the pushrod is accordingly in communication with the lumen 66 of the inner catheter 30. The outer sheath 24 and the inner catheter 30 can move relative to each other with the relative movement of the cylindrical body 70 and the pushrod 75.

Figure 7B:
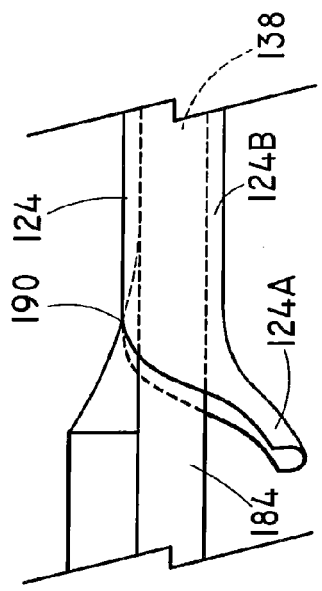
FIG. 7B is a detailed view of a portion of a splitter of the handle in FIG. 7A.
Figure 7C:
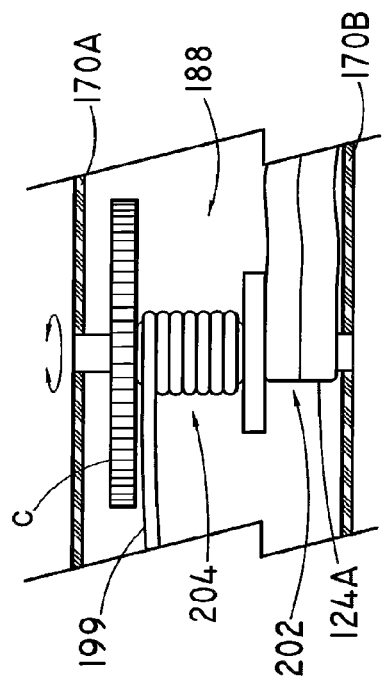
FIG. 7C is a detailed view of a portion of a rotatable mechanism of the handle in FIG. 7A.
Figure 7A:
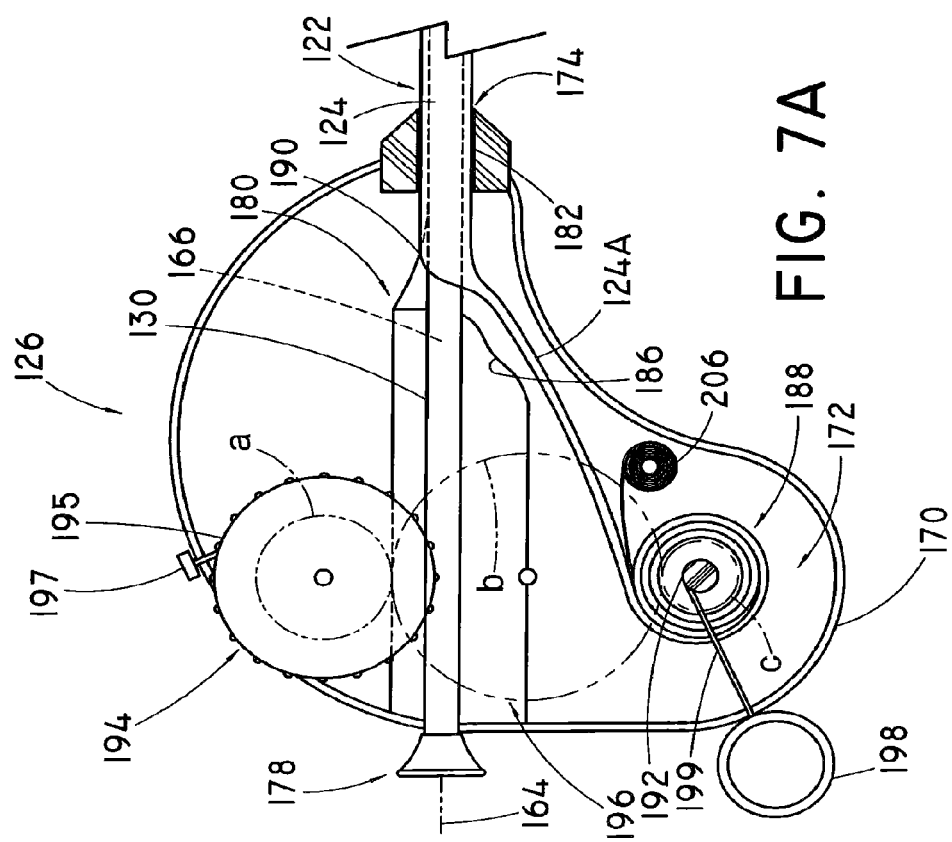
FIG. 7A is a side view of one embodiment of a handle of a stent deployment system.

FIGS. 7A-7C illustrate another embodiment of the handle that may be particularly useful for deploying lengthier medical devices. The handle 126 is a multi-component assembly, ergonomically designed, which includes a housing 170 defining a cavity 172. The housing 170 is preferably a two-part molded plastic, such as ABS (acrylonitrile, butadiene, styrene), that can be snap-fit together, although the housing 170 could be molded from different polymers and/or plastics. Optionally, the handle 126 can include a port 174 for receiving a tubular member within the housing cavity 172. A port 178 can also be included to permit the introduction of fluid and/or a guide wire.

The handle 126 can include a splitter 180 configured to slice a tubular member having a wall defining a lumen. Although reference will be made to the outer sheath 124 of the stent deployment system with the rolling liner described herein as an example of the tubular member, it can be appreciated that the splitter 180 can be used with other tubular members without the use of the rolling liner. The splitter 180 can be disposed within the housing cavity 172, and in a position to engage with the outer sheath 124. A channel 182 may be disposed between the port 174 and the splitter 180 and configured to guide the outer sheath 124 to the splitter 180. The splitter 180 may also include a guiding member 184 disposed within the lumen 138 of the outer sheath 124 and configured to guide the outer sheath 124 to the splitter 180. The guiding member 184 may extend in a distal direction within the lumen 138 of a nonsliced portion 124B of the outer sheath 124. The splitter 180 may also include a guiding edge 186 configured to guide the sliced portion 124A of the outer sheath away from the splitter 180. The guiding edge may be constructed as a channel or slot in order to better flatten the sliced outer sheath.

The splitter 180 preferably includes a cutting edge 190. The cutting edge 190 may be sized and configured to split the outer sheath 124, which may include the outer layer, the structural layer, such as a metallic layer, and/or the rolling liner, as described above. Further, when the sealing mechanism or like member is provided distal of the splitter with the outer sheath 124, the splitter 180 may also split or slice the sealing mechanism. In another embodiment, a proximal portion of the outer sheath 124 does not include a structural layer and would permit the cutting edge to slice the outer sheath more easily. As shown in FIG. 7B, the outer sheath 124 can be sliced axially along a portion of the wall of the outer sheath 124 from the proximal end along a distal direction to form a sliced portion 124A from the unsliced portion 124B of the outer sheath 124. In one example, the cutting edge 190 is a scalpel blade securably attached to the guiding member 184. The cutting edge may be curved or angled at a preferred degree (e.g., 0-90 degrees and preferably 30-60 degrees) to better cut the outer sheath, or even serrated.

In one embodiment, the handle 126 includes a rotatable mechanism 188. The rotatable mechanism 188 can have a spool portion 192 to wind the sliced portion 124A of the outer sheath 124. The sliced portion 124A of the outer sheath 124 can be pre-attached to the spool portion during manufacturing. The rotatable mechanism 188 can be rotatably mounted within the housing cavity 172. For example, the rotatable mechanism can be a shaft that can rotate about an axle within the housing cavity. In some embodiments, the rotatable mechanism 188 is pre-tensioned with a spring for automatic winding capabilities in order to retract the outer sheath. This can reduce the amount of force the operator must exert when retracting the outer sheath. The spring force needed to retract the outer sheath and slide it against the splitter can vary depending on the length of retraction required for deployment of the tubular medical device, the wall thickness and wall constructions of the outer sheath, the type of tubular medical device (coated stent, bare stent, covered stent, etc.), etc. The force is initially high to overcome static forces due to the outer sheath surrounding the entire tubular medical device and to the capability of cutting through the structural reinforcement. Once the initial static force is overcome, the force required to continue retracting the outer sheath and splitting the outer sheath is much less. For example, it has been found that for a 200 mm stent, 45 N was initially require to begin retracting the outer sheath and 20 N was required after an initial period.

The rotatable mechanism 188 can be coupled to a control mechanism 194. The control mechanism 194 can urge the rotatable mechanism 188 to rotate in a direction suitable to retract a portion of the outer sheath 124 into the housing cavity 172 and/or to wind the sliced portion 124A of the outer sheath 124 about the spool portion 192. The control mechanism 194 can include any number of mechanisms that can be manipulated by the operator. For example, the control mechanism 194 can be a thumbwheel, a trigger, a dial, a piston, a knob, a handle, or the like. The control mechanism 194 can be mechanically coupled to the rotatable mechanism 188 by any number of gears, pawls, ratchet wheels, sprockets, rack and pinion, or the like. For example, FIG. 7A illustrates the control mechanism 194 as a thumbwheel 195 that includes gear engaging members engageable with a gear system 196 with a series of gears a, b, c to control the rotatable mechanism 188. The gear system 196 is coupled to the gear engaging members of the thumbwheel 195 and can be rotated as the thumbwheel rotates. The gear ratio can be about 1:1 or about 1:2 or any suitable ratio known by one of ordinary skill in the art.

The handle 126 may also include a switch 197 or safety lock with a first position and a second position. The switch can operate in the first position to lock the control mechanism 194 and prevent the outer sheath 124 from retracting and winding. The switch 197 may also operate in the second position to enable the control mechanism 194 to operate freely, allowing a portion of the outer sheath 124 to retract and to wind about the spool assembly 188.

A pull handle 198 may also be included in the handle 126, which can be used to quicken the retraction of the outer sheath 124. In one example, the pull handle 198 can be connected to the sliced portion of the outer sheath. The pull handle 198 can be pulled to retract the outer sheath 124 away from the splitter 180. In other examples, the pull handle 198 can have a portion connected to a pull wire 199. The pull wire 199 can have a distal end attached to another portion of the spool portion 192 of the rotatable mechanism 188 and a proximal end disposed external to the housing cavity 172, preferably, connected to the pull handle 198. The pull handle can be a ring, a bar, a grip handle or the like. A portion of the pull wire 199 is wound around the spool portion 192, as shown in FIG. 7C. The proximal end of the pull wire 199 can be pulled to wind the sliced portion 124A of the outer sheath 124 and to retract the outer sheath 124 within the housing cavity 172.

In FIG. 7C, the rotatable mechanism 188 is connected between two sides 170A, 170B of the housing 170. The spool portion 192 may have a first annular region 202 for receiving the sliced portion 124A of the outer sheath and a second annular region 204 adjacent to the first annular region 202, for receiving the wound pull wire 199. Preferably, the second annular region 204 of the spool portion 192 is coupled to a one-way bearing. The one-way bearing can allow the winding of the sliced portion 124A of the outer sheath about the first annular region 202 without impacting or unwinding the pull wire 199 of the second annular region 204. Also shown is gear c of the gear system securably attached to the rotatable mechanism 188. It is appreciated that the shown embodiment of the rotatable mechanism 188 can be designed in various configurations, such as positioning the gear c in between the first and second annular regions 202, 204.

To increase the retraction force and speed of the outer sheath 124, a feed stock 206 can be rotatably mounted within the housing cavity 172 and inserted with the winding of the outer sheath for improved mechanical advantage. Preferably, the feed stock 206 is flattened material that is wound around a second rotatable mechanism. A portion of the feed stock can be inserted with the sliced portion 124A of the outer sheath while the sliced portion is being wound about the spool assembly 188. Since the feed stock is inserted between wound sliced portions of the outer sheath, the distance from the center to the edge of the wound sliced portion of the outer sheath increases more rapidly. Thus, for a given annular movement of the rotatable mechanism 188 there is greater length of the outer sheath 124 that will wind around the spool portion 192. The thickness of the feed stock can be uniform, such as 0.01 inches, or can be tapered or stepped at a suitable rate. The rate of tapering can be uniform, for example 0.01 inches per the circumference distance of the spool portion, or can vary as required to increase the retraction rate at the desired rate.

In one preferred embodiment, with reference to FIG. 7A, the handle 126 can be used with the deployment system described above. For example, the inner catheter 130 described above can be used as the guiding member. One embodiment of the cutting edge 190 is a scalpel blade that is securably attached to the inner catheter 130. The scalpel blade can be inserted into a preformed slot within the inner catheter 130 and attached with an adhesive. The scalpel blade can be heated to a temperature such that, when contacted to the inner catheter 130, the scalpel can be heat set into the wall of the inner catheter. Further, the cutting edge may be a plastic or other material with a sufficiently sharp edge to cut the outer sheath. The port 178 is in communication with the lumen 166 of the inner catheter. Accordingly, the outer sheath 124 can be retracted by rotating the thumbwheel 195 in a suitable direction to cause the rotatable mechanism 188 to rotate and to begin retracting the outer sheath 124. Retraction of the outer sheath causes the outer sheath to be sliced across the splitter 180, while the rotatable mechanism continues to rotate and wind the sliced portion of the outer sheath. Eversion of the rolling liner is thus achieved while the outer sheath is retracted and moved relative to the inner catheter 130 that is fixed within the housing 170. Other embodiments of outer sheaths with perforations or pre-weakened lines and/or handles are described in US Publs. 2007/0010867A1 to Carter et al., 2007/0244540 to Pryor, 2007/0219617A1 to Saint, which are incorporated herein by reference in their entirety.

Figure 8:
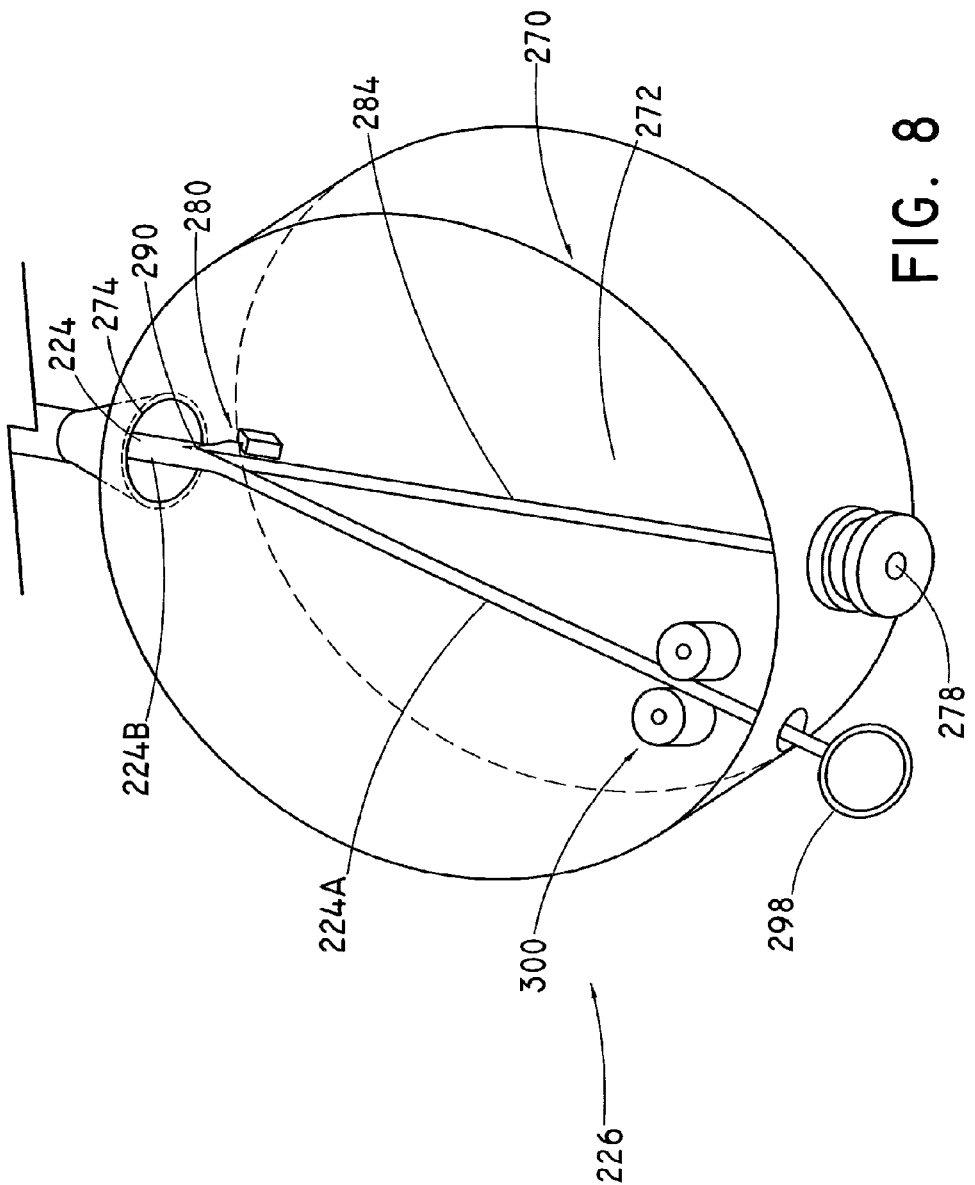
FIG. 8 is a perspective view of another embodiment of a handle of a stent deployment system.

FIG. 8 is a perspective view illustrating another handle 226. The handle 226 includes a housing 270 including a cavity 272. Also shown, the handle 226 can include a port 274 for receiving the outer sheath 224 within the housing cavity 272 and a port 278 that can be configured to be in communication with the lumen of the inner catheter or outer sheath. The port 278 can be used for the introduction of fluid and/or a guide wire. The handle 226 includes a splitter 280 configured to slice the outer sheath 224. A guiding member 284 may also be disposed within the lumen of the outer sheath 224 and configured to guide the outer sheath 224 to the splitter 280. The guiding member 284 may extend in a distal direction within the lumen of a nonsliced portion 224B of the outer sheath 224. The inner catheter described above can be used as the guiding member. The splitter 280 preferably includes a cutting edge 290. The cutting edge 290 includes substantially similar features as related to the cutting edge 190 described herein. The outer sheath 224 can be sliced axially along a portion of the wall of the outer sheath 224 from the proximal end along a distal direction to form a sliced portion 224A of the outer sheath 224. A pull handle 298 may be attached to the sliced portion 224A and is adapted to be pulled when the tubular medical device is ready to be deployed. The handle 226 may include a flattening mechanism 300 configured to flatten the sliced portion 224B before exiting the handle 226. The flattening mechanism 300 can include two or more wheels disposed and attached within the housing cavity 272, where a region between the two wheels is configured to receive the sliced portion 224A therebetween. The flattening mechanism can be disposed and attached to the housing along any portion of the sliced portion.

FIG. 9A is a side view illustrating yet another handle 326. The handle 326 includes a housing 330 defining a main lumen 332 and a branch lumen 334 that is angled off of the main lumen 332. Each of the main and branch lumen may have tapered walls whereby the cross-sectional area of the respective lumens increases in the proximal direction. The handle 326 can include a port 336 for receiving the catheter body 322 within the housing cavity 332 and a port 338 that can be configured to be in communication with the lumen 327 of the inner catheter 325. It is desirable that the proximal end of the inner catheter 325 be sealably engage with the region of the port 338 in order to minimize, if not eliminate, any leakage of fluid out of the main lumen 332.

The port 338 can be used for the introduction of fluid and/or a guide wire. FIG. 9B is a partial cross-sectional view of the handle 226. In FIG. 9B, the handle 326 include a cutting edge 340 configured to slice the outer sheath 324. Preferably, the cutting edge 340 is securably attached to the inner catheter 325 to face away from the direction of removal, and is shown to be wedged in the main lumen 332. This placement of the cutting edge helps it remain in place during the operation of removing the outer sheath. The inner catheter 325 aids in guiding the outer sheath 324 to the cutting edge 340. The cutting edge 340 includes substantially similar features as related to the cutting edges described herein. The outer sheath 324 can be sliced axially along a portion of the wall thereof from the proximal end along a distal direction to form a sliced portion 324A of the outer sheath 324.

A pull handle 342 may be attached to the sliced portion 324A and is adapted to be pulled when the tubular medical device is ready to be deployed. In FIG. 9A, the pull handle 342 is shown threadably attached to the handle 226, while FIG. 9C illustrates the removal and withdrawal of the pull handle 342. The withdrawal of the pull handle 342 in the direction shown by the arrow urges the wall of the outer sheath against the cutting edge. The pull handle 342 can be various shapes and sizes. It is desirable that the pull handle 342 be sealably and removably attached to the handle 326 in order for it to be secured thereto during delivery and in order to minimize, if not eliminate, any leakage of fluid out of the branch lumen 334. In one embodiment, a thin sleeve 343 is disposed coaxially around the body defining the branch lumen 334 and at least partially over the pull handle 342. The thin sleeve 343 is for protecting the operator from potential sharp edges of the tube and containing any fluid used in the catheter. The thin sleeve 343 may be shaped like an accordion to permit the sealing function regardless of the position of the pull handle 342. As shown in FIG. 9D, the handle 326 may include a guiding wheel 344 configured to ease the withdrawal of the pull handle 342 and the sliced outer sheath 324A, especially when withdrawing at an angle with respect to the main lumen 332. In another embodiment shown in FIG. 9E, the pull handle is disposed parallel to the main lumen 332 and the port 338 is at the branch lumen 334. Thus, the sliced portion 324A extends along the main lumen 332 and out the proximal end thereof, while the inner catheter 325 is curved into the branch lumen 334. This configuration may permit the operator to pull more easily the sliced portion as the withdrawal force is entirely axial and not partially axial and angular as in FIG. 9B.

FIGS. 10A-10D illustrate another embodiment of the handle 426 incorporated some of the features described herein, which is similar to the handle 126 except as described below. The handle 426 includes a housing 470 defining a cavity 472. The handle 426 includes a strain relief portion 428 extending distally from the handle. The strain relief portion 428 can be tapered down to the diameter of the outer sheath 424. A trigger 430 is positioned on the handle and is adapted to start and stop the winding of the outer sheath 424. The trigger 430 may be positioned anywhere on the handle 426, and is preferably positioned along the top or bottom of the handle. A distal port 474 is provided for receiving at least the outer sheath 424 within the housing cavity 472, while the port is shown receiving the strain relief portion 428. A proximal port 478 can also be included to permit the introduction of fluid and/or a guide wire. The proximal port 478 is preferably at the proximal end of the handle 426, opposite the distal port, and in alignment with the distal port 474. Extending from the proximal portion 478 can be the proximal end of the inner catheter or a tubular extension 432 of the inner catheter, as shown, having a lumen in communication with the lumen of the inner catheter. The end 433 of the tubular extension 432 can be adapted for a luer connector or for fluid coupling, or alternatively a separate coupling can be attached to the end of the tubular extension.

Figure 10A:
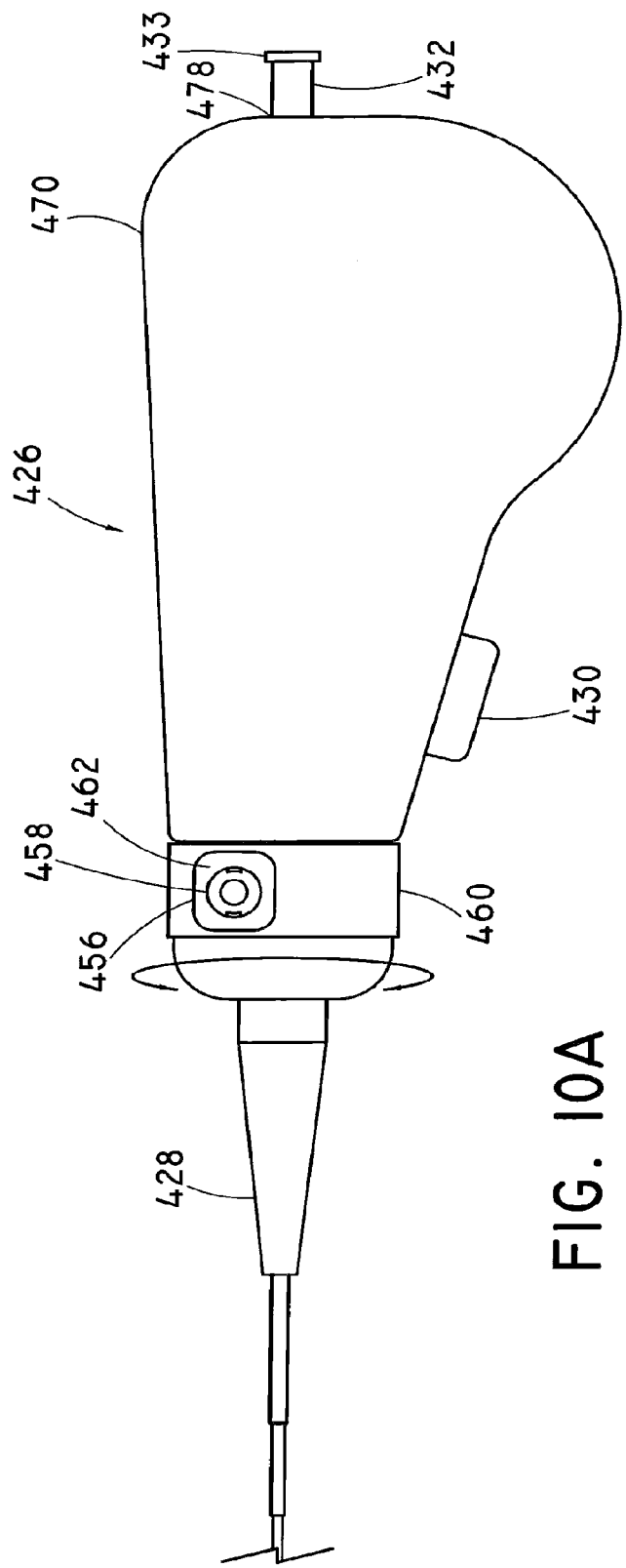
FIG. 10A is a side view of another embodiment of a handle of a stent deployment system.
Figure 10B:
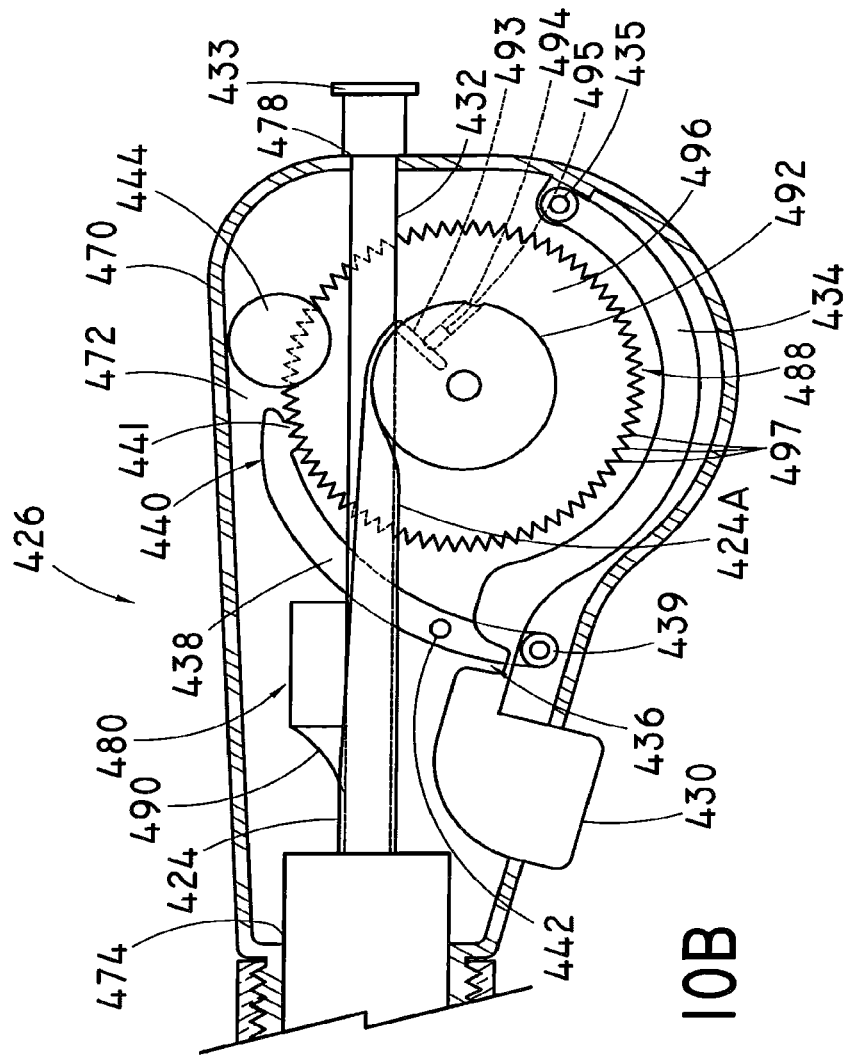
FIG. 10B is a side view of a portion of the handle of FIG. 10A, depicting the internal portion of the handle.
Figure 10C:
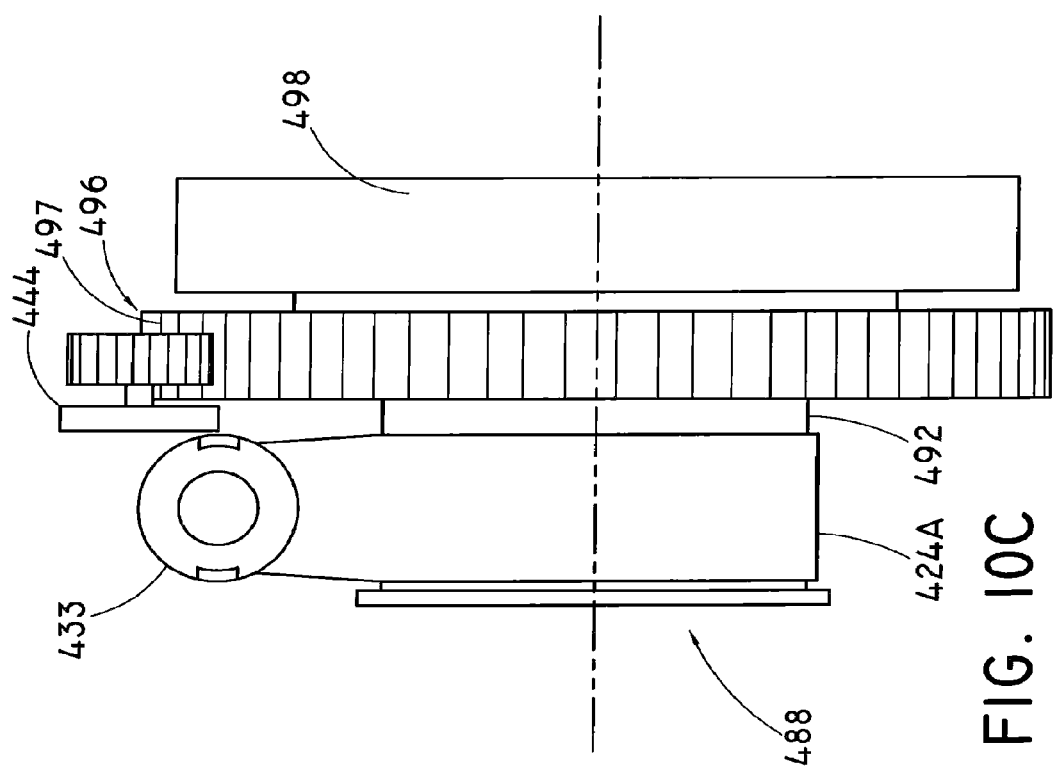
FIG. 10C is a detailed view of a portion of a rotatable mechanism of the handle in FIG. 10A.

The splitter 480 is attached to the tubular extension 432. The splitter 480 preferably includes the cutting edge 490. The cutting edge 490 may be sized and configured to split the outer sheath 424 longitudinally. The sliced portion 424A of the outer sheath may be guided and/or flattened before winding by the use of a guiding wheel, similarly positioned as wheel 344, mounting within the housing proximate the tubular extension. The rotatable mechanism 488 has the spool portion 492 capable of receiving the sliced portion 424A of the outer sheath when wound. The sliced portion 424A is preferably attached to the spool portion. For example, the spool portion 492 can include a radial groove 493 extending from an intermediate portion to the circumference of the spool portion. A tapped bore 494 in communication with the radial groove 493 is positioned at an angle to the groove 493 for receiving a set screw 495. The sliced portion 424A of the outer sheath 424 can be pre-attached to the spool portion 492 of the rotatable mechanism during manufacturing by passing its end through the radial groove 493, and tightening the set screw 495 to fix the end of the outer sheath therein. The rotatable mechanism 492 is pretensioned with a spring 498 of a sufficient size and force source to provide automatic winding capability for retracting the outer sheath. One preferred arrangement of the rotatably mechanism is shown in FIG. 10C.

The trigger 430 permits the rotatable mechanism 488 to rotate in a direction suitable to retract a portion of the outer sheath 424 into the housing cavity 472 and/or to wind the sliced portion 424A of the outer sheath about the spool portion 492. The trigger 430 is coupled to the gear 496 of the spool assembly 488 through one or more mechanical linkages. For example, FIG. 10B illustrates the trigger 430 including a trigger arm 434 that is pivotably attached to the housing 470 at an attachment end 435. The trigger arm 434 includes a slot 436 and can be biased with a spring to a position such that the trigger 430 has a steady state outward position, as shown in FIG. 10B. When the trigger 430 is pressed inward into the housing 470, the trigger arm 434 pivots inward about the attachment end 435. A pawl arm 438 is also pivotably attached to the housing at an attachment end 439. The pawl arm 438 includes an engaging end 440 with one or more teeth 441 sized to fit within the teeth 497 of the gear 496. A pin 442 extends laterally outward from the pawl arm 438 and is sized to be received in the slot 436 of the trigger arm 434. The pawl arm 438 is also biased with a spring to a position such that the engaging end 440 is in a steady state engagement position with the gear 436 to inhibit any rotation thereof. After the trigger 430 is pressed inward, the slot 436 receives the pin 442 of the pawl arm 438. The edges of the slot 436 are configured to urge the pin 442 to move in a position such that the pawl arm 438 pivots away from gear 496 and the engaging end 440 is disengaged from the gear 496 to allow the gear to rotate freely. A damper or rotational speed controller 444 can be engaged with the gear 496 to control the rotational speed of the gear. One or more rotational speed controllers may be used to control the gear at one or more speeds.

A way to flush the lumen of the inner catheter is to introduce flushing fluid through the end 433 of the tubular extension 432. Various port configurations at the distal region of the system are already described herein. To flush the annular lumen defined between the inner catheter and the outer sheath, the handle 426 can further include a tubular flushing component 450. The tubular flushing component 450 is coaxially positioned about the outer sheath 424 and can extend at least partially within the handle cavity 472, as well as partially over or within the proximal end of the strain relief portion 428, as shown in FIG. 10D. The tubular flushing component 450 defines a flushing chamber 452 between the outer surface of the outer sheath 424 and the luminal surface of the tubular flushing component 450. The flushing chamber 452 can be sealed at a proximal end and/or a distal end by one or more sealing rings 454 surrounding the outer sheath. A bore 456 extends radially through the wall of the tubular flushing component 450 for defining a flushing conduit 458 that extends radially outward from the outer sheath 424. A rotatable cap 460 can be provided adjacent the distal end of the handle 426 and coaxially about the distal portion of the tubular flushing component 450. The cap 460 has an opening 462, which, once the cap 460 is rotated into a predetermined position, the opening 462 is in alignment with the flushing conduit 458. The flushing conduit has an end adapted to be coupled to a fluid source. The outer sheath 424 can include an opening 464 in its wall to be is positioned within the flushing chamber 452 in order to receive flushing fluid and provide access to the annular lumen for flushing. Also, the rotation of the cap 460 can provide a safety feature that through mechanical linkage(s) may inhibit the trigger 430 from being pressed inward to initiate rotation of the rotatable mechanism. Additional connectors are shown within the strain relief portion 428 to provide strength and orientation to the outer sheath. It is appreciated by one skilled in the art that the exact position of each of the components and number of linkages are not critical to the invention, and that the components can be repositioned and the number of linkages can be increased or decreased to carry out the invention. It is also appreciated by one skilled in the art that electronic components may replace one or more of the components to carry out the same function.

As appreciated by one of ordinary skill in the art, the handles may incorporate one or more of the structural features discussed with any of the embodiments described above. It is understood, that although some embodiments of the handle are described above specifically in relation to the outer sheath and the stent deployment system, the handles may be used with other types of tubular devices as known in the art.

As can be seen in the handles with a splitter, e.g., in FIGS. 7A, 8, 9B, 9E, and 10B, a portion of the outer sheath is pre-split from its proximal end to a point where the outer sheath engages the splitter. This allows the proximal end of the outer sheath to be attached to the rotatable mechanism during manufacturing in order to provide a handle that is operable from packaging. Thus, during the medical procedure, the clinician can simply begin retracting the outer sheath relative to the inner catheter and winding the outer sheath around the rotatable mechanism. As mentioned previously, the initial force to begin splitting the structurally reinforced outer sheath can be high to overcome static forces. The clinician is then left with not only applying a retraction force to overcome the initial static forces, but also avoid a jerky or jolty retraction once the retraction force becomes much less after the initial period. One factor that contributes to the high static force is the initial slicing through the outer sheath. Hence, in order to reduce its contribution to the static force and thus reducing the overall initial static force, a portion of the outer sheath can be additionally modified.

Figure 11A:
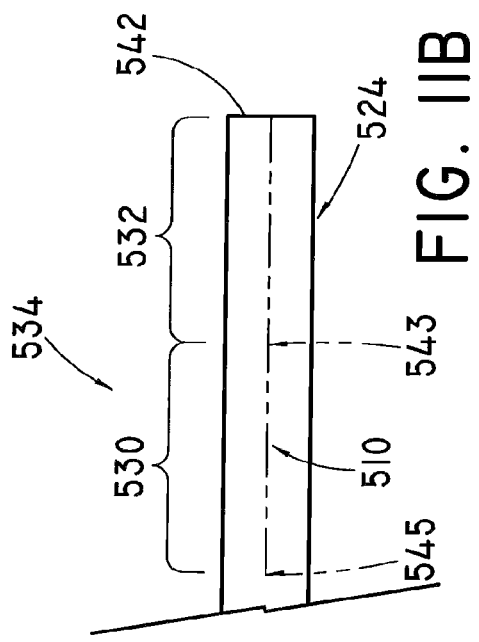
FIG. 11A is a top view of a portion of a stent deployment system, depicting an outer sheath with a weakened region next to a splitter of a handle.

FIGS. 11A-11E depict a weakened region 510 constructed in the outer sheath 524, and its method of manufacturing, that reduces the overall retraction force required to overcome the initial static forces. As shown in FIG. 11A, the weakened region 510 is preferably oriented longitudinally and in alignment with the splitter 515 during manufacturing. The longitudinal distance of the weakened region 510 is measured from the point 543 of engagement with the splitter 515 to another point 545 located distal thereto. In one example, the longitudinal distance of the weakened region 510 can be at least as long as the length of the tubular medical device to be deployed. In this instance, once the tubular medical device is deployed, the splitter 515 will engage a non-weakened region of the outer sheath 524 at point 545. However, in other examples, the longitudinal distance of the weakened region 510 can be less than the length of the tubular medical device to be deployed. In this other instance, it may be found that the most primary factor in the initial static force for retraction and deployment is due the interaction of the outer sheath 524 and the loaded tubular medical device. Thus, after a portion of the outer sheath 524 is initially removed from the tubular medical device during retraction and deployment, the retraction force becomes sufficiently less to continue retraction, as well as to slice through the outer sheath 524. The portion of the outer sheath removed from the tubular medical device can correlate to the longitudinal distance of the weakened portion 510, which can be represented as a percentage of the length of the tubular medical device. It can be at least approximately 10% for a single wall catheter, or at least approximately 110% for a everting catheter.

Figure 11B:
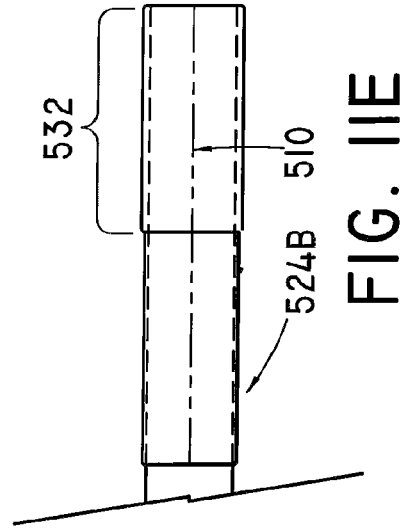
FIGS. 11B-11E are top views depicting a method of making a weakened region within an outer sheath.
Figure 11C:
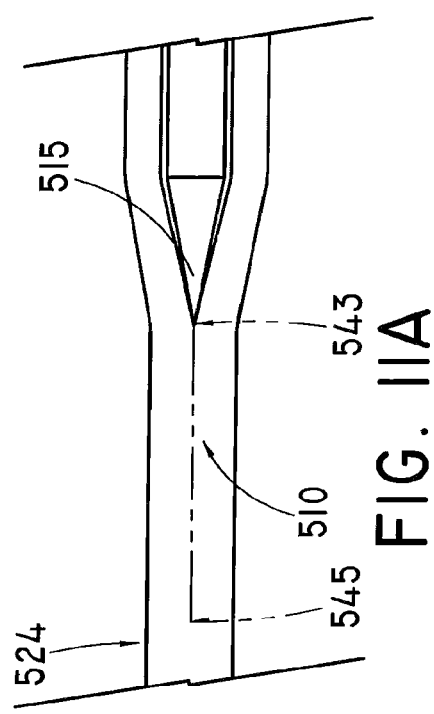
Figure 11E:
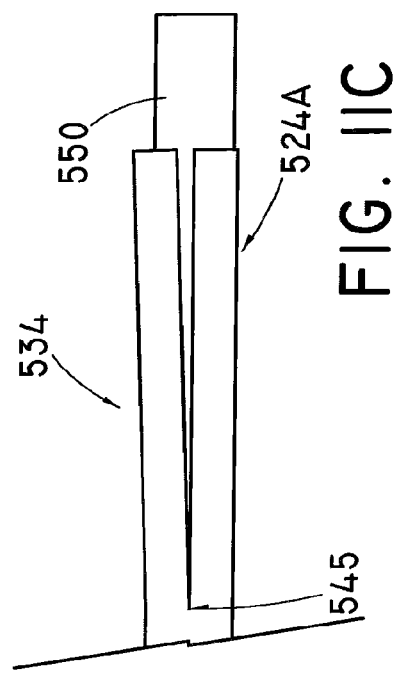
Figure 11D:
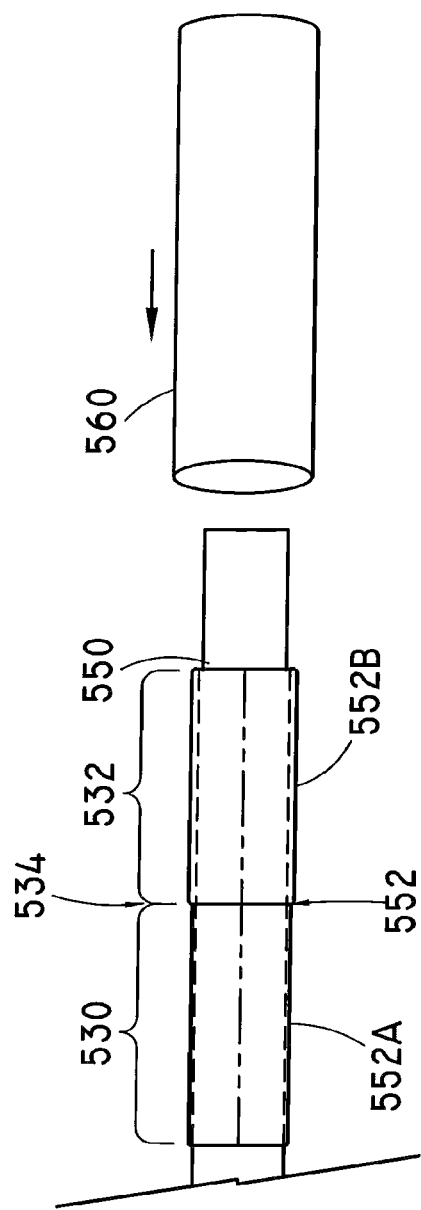

According to FIG. 11B, the weakened region 510 can be a longitudinal region 530 of the outer sheath wall that does not include a structural reinforcement. In other words, the longitudinal region 530 only contains one or more layers of polymers, which is easier to split there along than a longitudinal region with a structural reinforcement. One method of manufacturing this embodiment of the weakened region is to provide one embodiment of the outer sheath described herein, e.g., the proximal portion 45A shown in FIG. 4B. Here, the outer sheath has an outer layer, a structural reinforcement (a braid), and an inner layer. From the proximal end 542 of the outer sheath 524, a total longitudinal distance is measured to include the region 532 of the outer sheath 524 from its proximal end 542 to point 543 where the outer sheath will engage the splitter and include the longitudinal region 530 from point 543 at the splitter to point 545 to define the pertinent proximal region 534. The outer layer along the pertinent proximal region 534 may have a uniform thickness; however, this region may have a thinner outer layer similar to the distal end shown in FIG. 4B. According to FIG. 11C, the pertinent proximal region 534 is then sliced from the proximal end 542 of the outer sheath 524 to point 545 to define a pre-split outer sheath 524A. The pre-split outer sheath 524A is then placed on a mandrel 550. According to FIG. 11D, a layer 552 of outer layer material is placed to surround the pertinent proximal region 534. The layer 552 can be thicker material to add some tensile strength to the material for retraction so that it does not fail by axially separating, while thinner material may make the overall profile of the outer sheath more uniform and easier to split. It may be desirable to use both for the layer 552, such as a thinner material 552A (e.g., about 0.003-0.005 inches) for the longitudinal region 530 surrounding the weakened region 510 and a thicker material 552B (e.g., 0.005-0.009 inches) for the portion 532 proximal to the weakened region. It may also be desirable to use a layer 552 of a sufficient thickness to fill the split, while contributing a marginal, if any, to the overall diameter of the sheath. Heat shrink tubing 560 can then disposed around the pertinent proximal region 534, and a sufficient heat to melt the layer is applied to the assembly, which causes the outer layer material flow into the split of the pertinent proximal region. Alternatively, in some embodiments the layer 552 (552A, 552B) is not needed and the heat shrink tubing 560 can be applied directly to the pre-split outer sheath 524A to cause the outer layer material of the outer sheath to flow into the split. Further, reinforcement fibers, glass or carbon fibers, may be added to the outer sheath and/or any of the layers 552 before application of the heat shrinking tube 560 for added strength. The fibers can face in multiple directions, with some preferably radially bridging weakened region. Optionally, a strip of material of layer 552 (e.g., having a thickness of about 0.002-0.003 inches or more; and a lateral width of about 0.01-0.02 inches or more) comprising reinforcement fibers can be applied over the split before application of the heat shrink tubing. As shown in FIG. 11E, upon cooling and removal of the heat shrink tubing and the mandrel, the pre-split outer sheath is no longer split but a continuous structure 524B with the region that was formerly split containing the outer layer material, defining the weakened region 510 (shown as dashed lines). When the outer sheath 524B is attached to a handle with the splitter 515, the portion 532 proximal to the splitter may split again along the weakened region 510 for attachment to a portion of the handle. It can be appreciated by the skilled artisan that portion 532 proximal to the longitudinal region 530 surrounding the weakened region 510 need not be formed continuous as in FIG. 11D, but left pre-split as it is typically unnecessary to reattach the split of this region. Referring back to FIG. 11A, in operation, the splitter 515 can slice through the weakened region 510 of the outer sheath 524 more easily than when the outer sheath has a continuous structural reinforcement. This can reduce the contribution of the initial slicing of the outer sheath to the overall initial static force. Thus, the overall initial static force is reduced, making overall retraction of the outer sheath an easier and smoother operation, as well as avoiding jolts during retraction. It can be appreciated that any of the outer sheath embodiments described herein may include the weakened region 510, and that this weakened region can be used in combination with any of the handles discussed above. The weakened region 510 may even reduce the size of spring used in some of the handle embodiments.

Figures 12A, 12B, 12C:
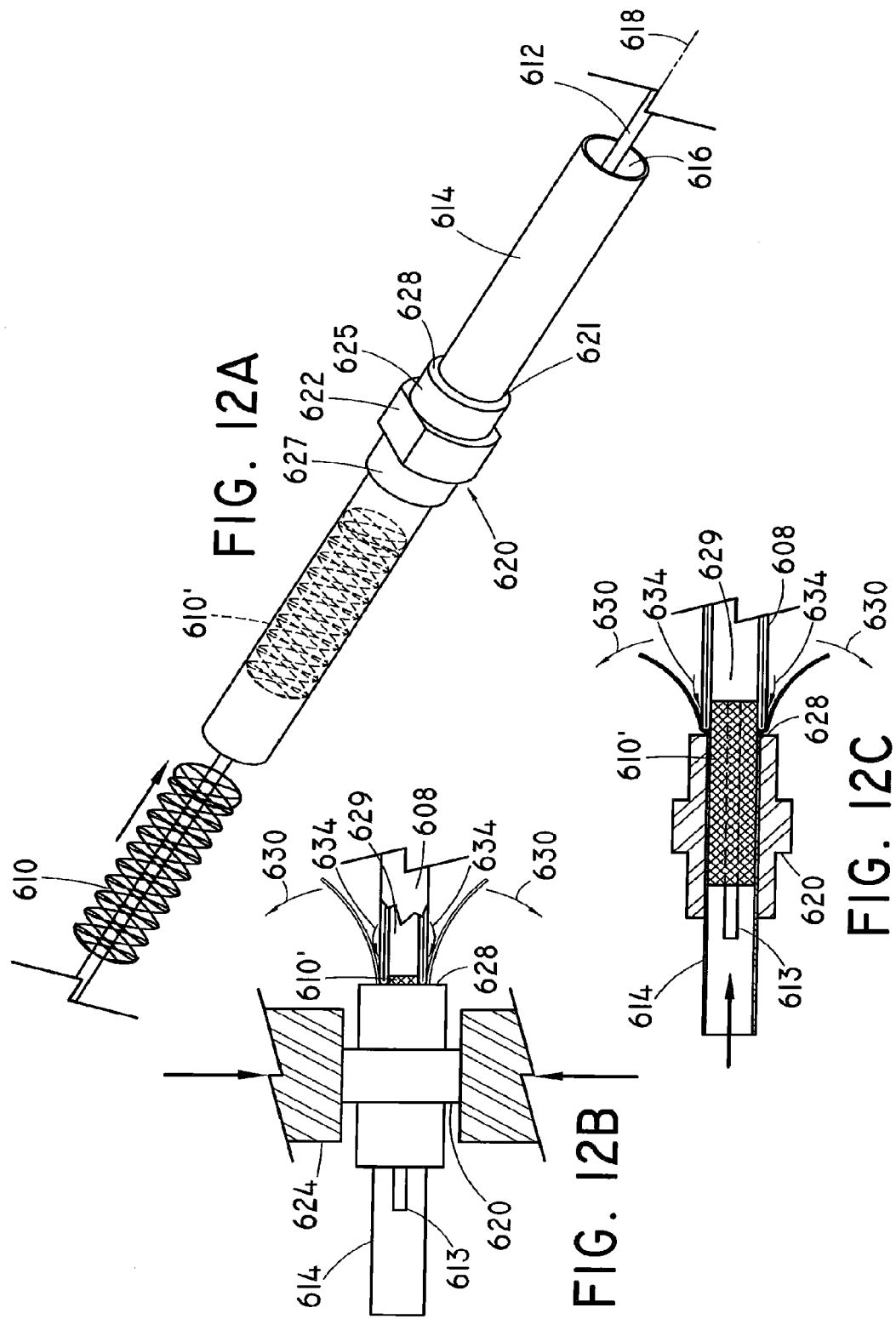
FIG. 12A is a perspective view of a stent loading system.
FIGS. 12B-12C are side views depicting a method of loading a tubular medical device with the stent loading system of FIG. 12A.

According to FIG. 12A-C, a device 600 for, and method of, loading the tubular medical device 610 into a stent deployment system 608, substantially similar to stent deployment system 20, is provided. With the inner catheter extending through the annular space of the outer sheath, the space of the stent retaining region is reduced thus making it more difficult to load a tubular medical device. Referring to the FIG. 12A, an inner mandrel 612 is extended through a tubular sleeve 614. The tubular sleeve 614 includes a lumen 616 about a longitudinal axis 618. Preferably, the tubular sleeve 614 comprises a flexible, easily tearable material, such as PTFE or other material with like characteristics; however, the material of the tubular sleeve should possess enough hoop strength to retain a loaded tubular medical device. The tubular sleeve 614 with the inner mandrel 612 extending therethrough is inserted through a lumen 621 of a fitting 620. The fitting 620 is preferably made of a durable material and has surfaces 622 that are configured to securably engage with a clamping mechanism 624.

The fitting 620 preferably has a luminal cross-sectional area that is slightly less than the cross-sectional area of the lumen of the tubular sleeve 614. The smaller cross-sectional area of the fitting lumen can further compress the tubular medical device 610 to a smaller cross-sectional area before being loaded into the stent deployment system. As shown in the Figures, the fitting 620 has a larger cross-sectional area in the middle portion 623 with smaller cross-sectional area portions 625, 627 extending axially therefrom. The middle portion 623 preferably has flattened portions in order to clamp better the fitting in a fixed location. The ends 628 of the axial extended portions 625, 627 may be chamfered to provide an angled surface from which to pull the tubular sleeve 614 when tearing.

According to FIG. 12A, the tubular medical device 610 in the compressed configuration is then inserted over the inner mandrel 612 and into the lumen 616 of the tubular sleeve 614. The inner mandrel 612 functions as a guiding member for the insertion of the tubular medical device 610. The loaded tubular medical device 610' is positioned within the fitting lumen 621. After positioning, the inner mandrel 612 can then be removed.

According to FIG. 12B, the inner catheter 613 of the stent deployment system 608 can be fully extended to unroll the rolling liner. The fitting 620 can be affixed or clamped by the clamping mechanism 624. The tubular sleeve 614 can be partially torn away or split. The stent deployment system 608 is maintained in the lumen 616 of the partially torn tubular sleeve 614. In FIG. 12B, the tubular sleeve 614 can be torn away against the end 628 of the fitting 620, represented by arrows 630, until a portion of the loaded tubular medical device 610' is exposed. Because the tubular medical device 610' is radially expanded against the luminal wall of the tubular sleeve 614, translational movement of the tubular sleeve 614 urges the translational movement of the tubular medical device 610' in that same direction. As a result, the tearing of the tubular sleeve 614 against the end 628 of the fitting 620 causes the tubular medical device 610' to move toward the end 628. Once a small portion of the tubular medical device 610' is exposed, the small portion can be inserted into the annular space 629 of the stent deployment system 608. The annular space 629 can have a cross-sectional area at least the same as or larger than the cross-sectional area of the fitting lumen 621. The most distal end of the stent deployment system 608 can be initially flared in order to receive the tubular medical device. As the tubular sleeve 614 continues to be torn to advance the tubular medical device 610', while the rolling liner 632 is rolled inwardly, as represented by arrows 634, the tubular medical device 610' is received into the annular space 629. FIG. 12C illustrates that by continuing to tear the tubular sleeve 614 and roll the rolling liner 632, the tubular medical device 610' can be fully loaded into the stent deployment system 608.

In accordance with the provisions of the patent statutes, the present invention has been described in what is considered to represent its preferred embodiment. However, it should be noted that the invention can be practiced otherwise than as specifically illustrated and described.

The invention claimed is:

1. A handle for a stent deployment system having a tubular member with a wall defining a lumen about a longitudinal axis between a proximal end and a distal end, the handle comprising:
   a housing including a cavity and a port configured to receive said tubular member within the housing cavity;
   a splitter disposed within the housing cavity and configured to slice said tubular member axially along the wall of said tubular member, wherein said tubular member is sliceable in a distal direction to form a sliced portion of said tubular member, wherein the splitter includes a cutting edge configured to slice the wall of the tubular member; and
   a guiding member having a portion disposed within the lumen of said tubular member, configured to guide said tubular member to the splitter, wherein the guiding member extends distally through a majority of the lumen of the tubular member from the cutting edge;
   wherein the cutting edge is securely attached to the guiding member.

2. The handle of claim 1, wherein the splitter includes a guiding edge configured to guide the sliced portion of said tubular member controllably away from the splitter.

3. The handle of claim 1, further comprising a tubular flushing component having a flushing chamber in communication with a side opening in said tubular member, said flushing chamber being defined by a proximal sealing ring and a distal sealing ring.

4. The handle of claim 1, further comprising a rotatable mechanism attached to said tubular member and rotatably mounted within the housing cavity, wherein rotation of the rotatable mechanism retracts a portion of said tubular member into the housing cavity and winds the sliced portion about the rotatable mechanism.

5. The handle of claim 4, wherein the rotatable mechanism is pre-tensioned with a spring force sufficient to retract said tubular member.

6. The handle of claim 4, further comprising a control mechanism coupled to the rotatable mechanism, wherein the control mechanism is configured to regulate the rotation of the rotatable mechanism.

7. The handle of claim 4, further comprising a switch with a first position and a second position, wherein the switch is operable in the first position to lock the control mechanism and inhibit rotation of the rotatable mechanism, wherein the switch is operable in the second position to enable rotation of the rotatable mechanism.

8. The handle of claim 4, further comprising a rotational speed controller to control the speed of rotation of the rotatable mechanism.

9. The handle of claim 4, further comprising a flattening mechanism configured to flatten the sliced portion of said tubular member before being wound about the rotatable mechanism, the flattening mechanism positioned within the housing along a portion of the sliced portion of said tubular member.

10. The handle of claim 9, wherein the flattening mechanism comprises two wheels configured to receive the sliced portion therebetween.

11. The handle of claim 1, further comprising a pull handle having a portion attached to a portion of the sliced portion of said tubular member, the pull handle disposed external to the housing cavity, wherein retraction of the pull handle retracts said tubular member within the housing cavity.

12. The handle of claim 1, wherein a distal portion of the tubular member includes a structural layer and a proximal portion of the tubular member does not include a structural layer, the splitter slicing through the proximal portion to slice more easily.

13. A handle for a stent deployment system having a tubular member with a wall defining a lumen about a longitudinal axis between a proximal end and a distal end, the handle comprising:
   a housing including a cavity and a port configured to receive said tubular member within the housing cavity; and
   a splitter disposed within the housing cavity and configured to slice said tubular member axially along the wall of said tubular member, wherein said tubular member is sliceable in a distal direction to form a sliced portion of said tubular member;
   further comprising a rotatable mechanism attached to said tubular member and rotatably mounted within the housing cavity, wherein rotation of the rotatable mechanism retracts a portion of said tubular member into the housing cavity and winds the sliced portion about the rotatable mechanism; and
   further comprising a supply of feed stock material and means for winding the sliced portion of said tubular member and the feed stock on said rotatable mechanism together, such that the sliced portion and the feed stock overlap wherein the feedstock is disposed within windings of the sliced portion.

14. A handle for a stent deployment system having a tubular member with a wall defining a lumen about a longitudinal axis between a proximal end and a distal end, the handle comprising:
   a housing including a cavity and a port configured to receive said tubular member within the housing cavity; and
   a splitter disposed within the housing cavity and configured to slice said tubular member axially along the wall of said tubular member, wherein said tubular member is sliceable in a distal direction to form a sliced portion of said tubular member;
   further comprising a rotatable mechanism attached to said tubular member and rotatably mounted within the housing cavity, wherein rotation of the rotatable mechanism retracts a portion of said tubular member into the housing cavity and winds the sliced portion about the rotatable mechanism; and
   further comprising a pull wire having a distal end attached to the rotatable mechanism and a proximal end disposed external to the housing cavity, a portion of said pull wire being wound around a spool assembly of the rotatable mechanism, wherein retraction of the proximal end of the pull wire rotates the rotatable mechanism to retract said tubular member within the housing cavity.

15. The handle of claim 14, further comprising a control mechanism coupled to the rotatable mechanism, the control mechanism being configured to regulate the rotation of the rotatable mechanism, wherein the pull wire is coupled to a one-way bearing allowing the control mechanism to wind the sliced portion about the rotatable mechanism without unwinding the pull wire.

\* \* \* \* \*